United States Patent
Sako

(10) Patent No.: US 7,852,332 B2
(45) Date of Patent: Dec. 14, 2010

(54) MEDICAL IMAGE PROCESSING AND DISPLAY APPARATUS INCLUDING ASSOCIATED PROCESSING AND CONTROL METHODS

(75) Inventor: Tsukasa Sako, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 705 days.

(21) Appl. No.: 11/202,016

(22) Filed: Aug. 11, 2005

(65) Prior Publication Data

US 2006/0033728 A1    Feb. 16, 2006

(30) Foreign Application Priority Data

Aug. 11, 2004    (JP)    .............................. 2004-234354

(51) Int. Cl.
*G06T 15/00*    (2006.01)
(52) U.S. Cl. ..................................................... 345/419
(58) Field of Classification Search ........................ None
See application file for complete search history.

(56) References Cited

U.S. PATENT DOCUMENTS

| | | | | |
|---|---|---|---|---|
| 5,452,416 | A | 9/1995 | Hilton et al. ................. | 395/161 |
| 5,570,404 | A | 10/1996 | Liang et al. ..................... | 378/8 |
| 5,825,908 | A * | 10/1998 | Pieper et al. ................. | 382/131 |
| 6,081,267 | A | 6/2000 | Stockham et al. ........... | 345/342 |
| 6,424,692 | B1 * | 7/2002 | Suzuki ........................... | 378/4 |
| 6,603,868 | B1 * | 8/2003 | Ludwig et al. .............. | 382/128 |
| 6,690,371 | B1 | 2/2004 | Okerlund et al. | |
| 2002/0090119 | A1 * | 7/2002 | Saito et al. ................... | 382/128 |
| 2004/0027359 | A1 * | 2/2004 | Aharon et al. .............. | 345/619 |
| 2004/0161139 | A1 * | 8/2004 | Samara et al. .............. | 382/131 |

FOREIGN PATENT DOCUMENTS

| | | |
|---|---|---|
| EP | 0981109 A | 2/2000 |
| JP | 07-014030 | 1/1995 |
| JP | 08-166995 | 6/1996 |
| JP | 2000-051202 A | 2/2000 |
| JP | 2001-319220 A | 11/2001 |
| JP | 2002-085355 A | 3/2002 |
| JP | 2002-229537 | 8/2002 |
| JP | 2004-215961 A | 8/2004 |
| WO | WO 03/045243 | 6/2003 |
| WO | WO 03/071779 | 8/2003 |

OTHER PUBLICATIONS

The above references were cited in a Jul. 4, 2008 Japanese Office Action issued in the counterpart Japanese Patent Application 2004-234354, which is enclosed.

* cited by examiner

*Primary Examiner*—Kee M Tung
*Assistant Examiner*—Edward Martello
(74) *Attorney, Agent, or Firm*—Cowan, Liebowitz & Latman, P.C.

(57) ABSTRACT

Range information associated with the range of an image group of a plurality of image which is to be displayed is designated. The designated range information is stored. Image processing is performed for each image of the image group corresponding to the stored range information to generate a display image group. The images of the generated display image group are switched to display an image on a display unit.

13 Claims, 16 Drawing Sheets

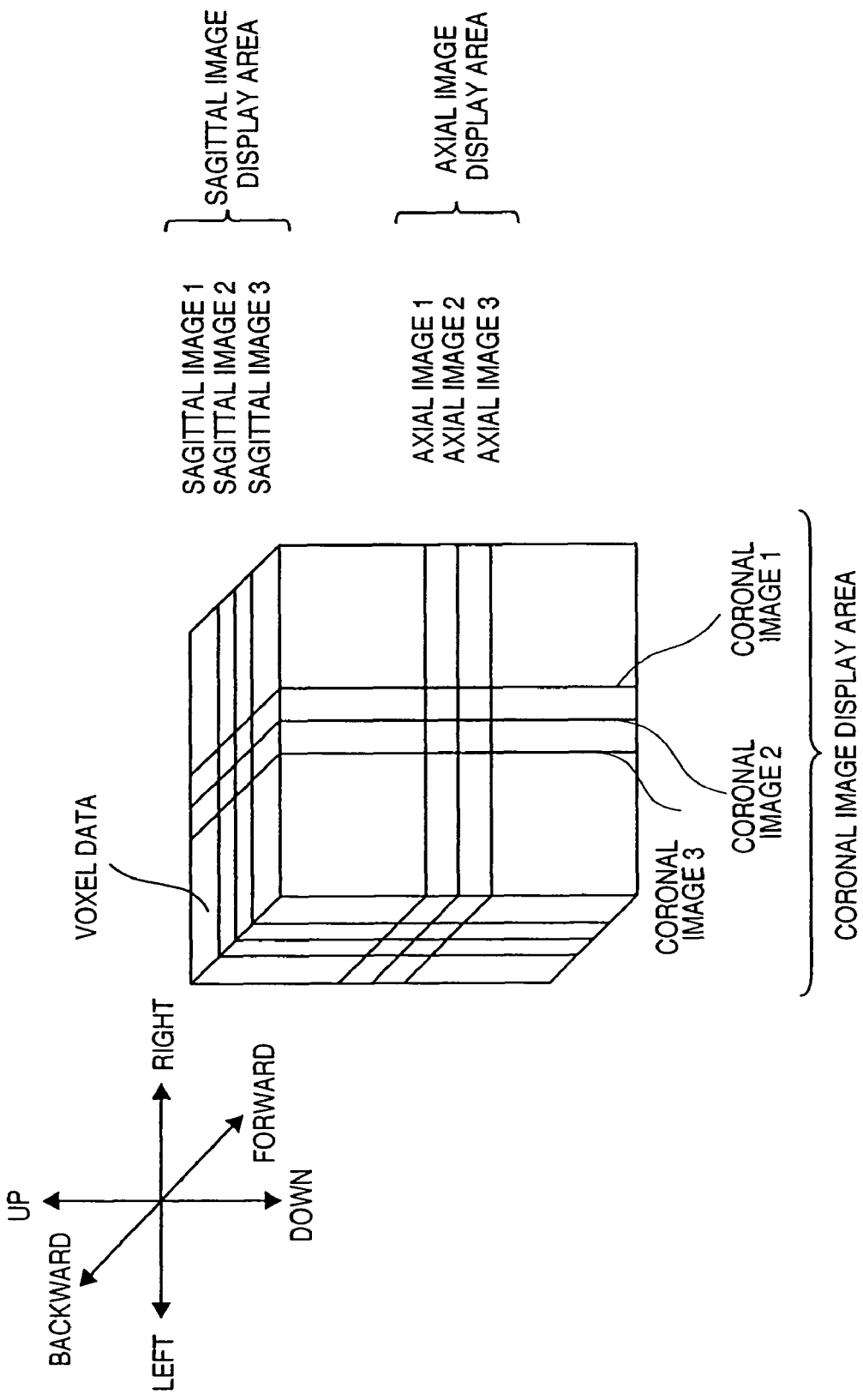

MEDICAL IMAGE PROCESSING AND DISPLAY APPARATUS INCLUDING ASSOCIATED PROCESSING AND CONTROL METHODS

FIELD OF THE INVENTION

The present invention relates to an image processing apparatus which switches a plurality of consecutive images to display an image, a control method therefor, and a program.

BACKGROUND OF THE INVENTION

Recently, in the field of radiographic techniques of taking radiographic images such as CT images and medical X-ray moving images, slight differences between a plurality of diagnosis target images such as multislice CT images have become important for diagnosis. Such images are displayed on a monitor to perform diagnosis.

A display method called a cine mode is available as a conventional technique in a medical image display method which handles many images as process targets, e.g., CT images and medical X-ray moving images. This method is a technique of dynamically switching a plurality of images to display an image, and is disclosed in Japanese Patent Laid-Open No. 8-166995.

There has also been available a technique of performing diagnosis by switching a currently displayed image to preceding and succeeding images within the same area by mouse and keyboard operations.

A RaySum display method or the like (e.g., Japanese Patent Laid-Open No. 7-014030) is also available, in which the image obtained by multiple time averaging of a plurality of images is displayed in order to reduce noise in each image and reduce the number of diagnosis images.

The above display method based on the cine mode is designed to only unitarily display by switching tomographic cross sections and consecutive images in slice order. In order to find slight differences between images, it is necessary to perform subtle comparison between the images. That is, the simple cine mode is designed to only sequentially switch image to display an image, and hence cannot perform subtle comparison between the images.

In the RaySum display method, the details of a plurality of slices are lost.

Switching with mouse and keyboard operations requires manual operation. That is, cumbersome operation is required.

SUMMARY OF THE INVENTION

The present invention has been made to solve the above problems, and has as its object to provide an image processing apparatus which can realize easy and precise observation of an image group, of a large number of image groups, which falls within a target range, a control method therefor, and a program.

According to the present invention, the foregoing object is attained by providing an image processing apparatus which switches a plurality of images to display an image, comprising:

designate means for designating range information associated with a range of an image group of the plurality of images which are to be displayed;

storage means for storing the range information designated by the designate means;

image generation means for generating a display image group by performing image processing for each image group corresponding to the range information stored in the storage means; and display control means for switching display image groups generated by the image generation means to display an image on a display unit.

In a preferred embodiment, the designate means designates, as the range information, start image identification information of a start image of the range and a range image count equivalent to the range, and the storage means stores the start image identification information and the range image count as the range information.

In a preferred embodiment, the apparatus further comprises control means for controlling a change made by the designate means, and the control means, when a change of the range of the image group to be displayed is to be executed by changing the start image identification information using the designate means, controlling the change such that the ranges before and after the change become continuous.

In a preferred embodiment, when a change of the start image identification information is to be executed by the designate means, the control means controls the change such that an image count from an image corresponding to the start image identification information before the change to an image corresponding to the start image identification information after the change falls within the range image count.

In a preferred embodiment, the apparatus further comprises timer means for generating a timer event, wherein the display control means repeatedly executes displaying, on the display unit, the display image group consecutively arranged in the range of the range image count while sequentially switching the images in the arranging order of the images in a forward direction in accordance with the timer event.

In a preferred embodiment, the apparatus further comprises timer means for generating a timer event, wherein the display control means repeatedly and alternately executes displaying, on the display unit, the display image group consecutively arranged in the range of the range image count while sequentially switching the images in the arranging order of the images in a forward direction in accordance with the timer event, and displaying, on the display unit, the display image group while sequentially switching the images in the arranging direction in a backward direction.

In a preferred embodiment, image processing executed by the image generation means includes gradation processing and enlargement/reduction processing.

In a preferred embodiment, when a change of the start image identification information is executed by the designate means, start image identification information before the change which is stored in the storage means is updated to start image identification information after the change.

In a preferred embodiment, the designate means further designates an image processing method for image processing to be executed with respect to images in a predetermined range which includes at least one image of an image group corresponding to the range information, and the image generation means generates a display image by performing image processing for the images in the predetermined range by using the image processing method designated by the designate means.

In a preferred embodiment, the image processing method includes image processing of generating an average image of images in the predetermined range by performing averaging processing for each of corresponding pixels between the images in the predetermined range.

In a preferred embodiment, the image processing method includes image processing of generating an MIP (Maximum Intensity Projection) image of a predetermined number of images in the predetermined range by using a maximum pixel value of each of corresponding pixels between the images in the predetermined range.

In a preferred embodiment, the apparatus further comprises timer means for generating a timer event, wherein the image generation means sequentially switches images as start images in the predetermined range, performs image processing for an image group in each predetermined range in which the switched image serves as a start image, and generates a display image corresponding to each predetermined range, and the display control means alternately and repeatedly executes displaying, on the display unit, display images corresponding to the each predetermined range which are arranged in the range of the range image count while sequentially switching the images in an arranging order in a forward direction with respect to a start image in the each predetermined range, and displaying, on the display unit, the images while sequentially switching the images in the arranging order in a backward direction.

In a preferred embodiment, the plurality of images include at least one cross section image group of three cross section image groups in arbitrary orthogonal directions crossing solid data.

In a preferred embodiment, the apparatus further comprises timer means for generating a timer event, wherein the image generation means generates a display image group by performing image processing for each image of at least one cross section image group of the three cross section image groups corresponding to range information stored in the storage means in accordance with the timer event.

According to the present invention, the foregoing object is attained by providing an image processing apparatus which switches a plurality of images to display an image, comprising:

setting means for setting an image range to be displayed in accordance with start image identification information and an image count;

display control means for performing display control to repeatedly display images included in the image range in a predetermined order; and image range changing means for changing the image range by changing the start image identification information.

According to the present invention, the foregoing object is attained by providing a control method for an image processing apparatus which switches a plurality of images to display an image, comprising:

a setting step of setting an image range to be displayed in accordance with start image identification information and an image count;

a display control step of performing display control to repeatedly display images included in the image range in a predetermined order; and an image range changing step of changing the image range by changing the start image identification information.

According to the present invention, the foregoing object is attained by providing a control method for an image processing apparatus which a plurality of images to display an image, comprising:

a designating step of designating range information associated with a range of an image group of the plurality of images which are to be displayed;

a storage step of storing the range information designated in the designating step in a storage unit;

an image generating step of generating a display image group by performing image processing for each image group corresponding to the range information stored in the storage unit; and a display control step of switching display image groups generated in the image generating step to display an image on a display unit.

According to the present invention, the foregoing object is attained by providing a program for realizing control of an image processing apparatus which switches a plurality of images to display an image, comprising:

a program code for a designating step of designating range information associated with a range of an image group of the plurality of images which are to be displayed;

a program code for a storage step of storing the range information designated in the designating step in a storage unit;

a program code for an image generating step of generating a display image group by performing image processing for each image group corresponding to the range information stored in the storage unit; and a program code for a display control step of switching display image groups generated in the image generating step to display an image on a display unit.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 1C is a view for explaining cross section images according to the first embodiment of the present invention;

DETAILED DESCRIPTION OF THE PREFERRED EMBODIMENTS

Preferred embodiments of the present invention will be described in detail in accordance with the accompanying drawings.

First Embodiment

Figure 1A:
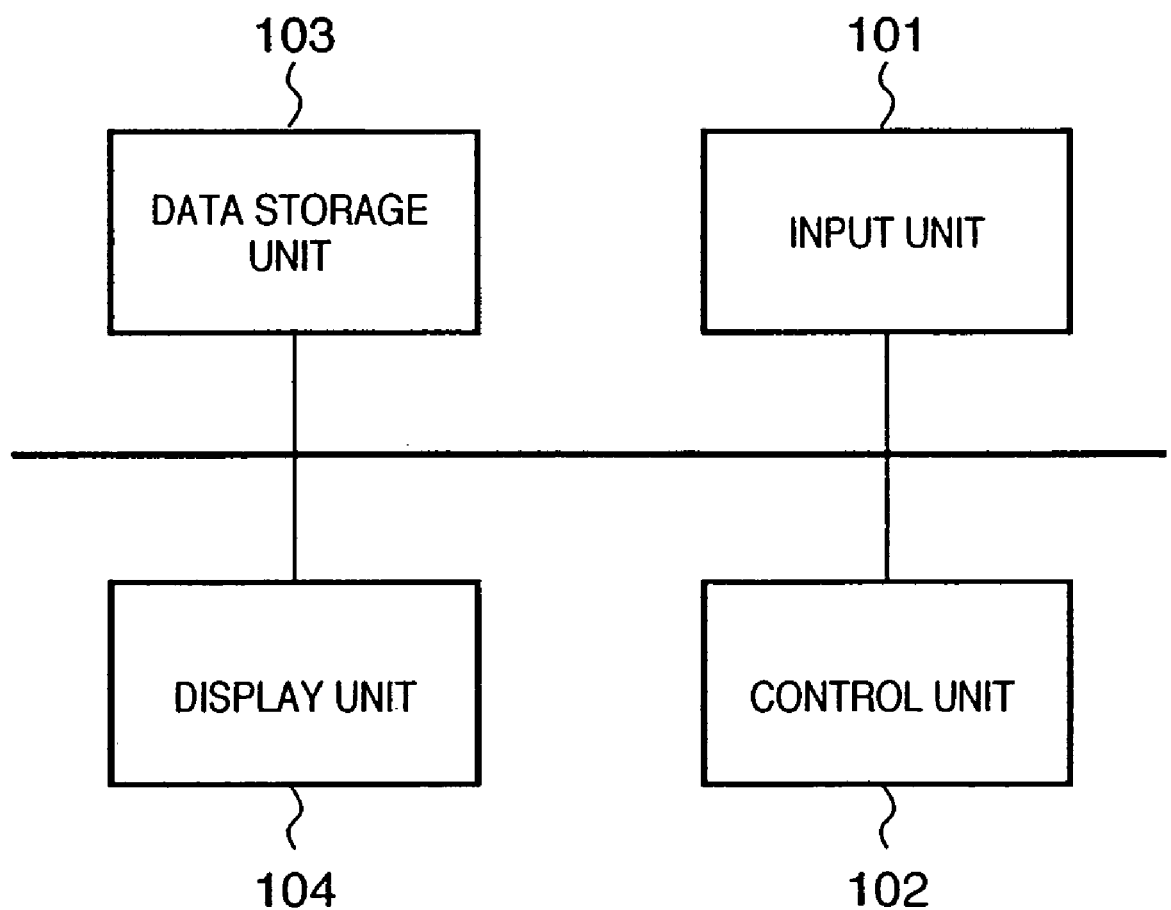
FIG. 1A is a block diagram for explaining the hardware arrangement of a radiographic image processing apparatus according to the first embodiment of the present invention.

FIG. 1A is a block diagram for explaining the hardware arrangement of a radiographic image processing apparatus according to the first embodiment of the present invention.

Referring to FIG. 1A, reference numeral 101 denotes an input unit such as a mouse or keyboard used to input instructions to a control unit 102. The control unit 102 controls the respective units on the basis of instructions input from the input unit 101. Reference numeral 103 denotes a data storage unit which is formed from a storage medium such as a hard disk or external storage medium and holds data. Radiographic images as process targets to be described later are stored in the data storage unit 103. Reference numeral 104 denotes a display unit such as a CRT or liquid crystal display which displays data, images, and the like.

The input unit 101, control unit 102, data storage unit 103, and display unit 104 are connected to each other through a system bus. In addition to CPU, the control unit 102 comprises a memory (e.g., a ROM) for storing various kinds of parameters and data for processing and a memory (e.g., a RAM) functioning as a data work area.

In this embodiment, an X-ray image will be exemplified as a radiographic image. However, the present invention is not limited to this. The present invention can also be applied to images sensed by other types of radiations.

Depending on the application or purpose, the radiographic image processing apparatus may be connected to a network to transmit/receive process target images from an external device through the network.

In addition, an imaging unit which performs radiography (using, for example, X-rays) may be connected to the radiographic image processing apparatus to store, in the data storage unit 103, radiographic images obtained by the imaging unit as process target images. Note that this imaging unit may have a general arrangement (e.g., that of a radiation generator or radiation sensor) for radiography.

An example of a GUI (Graphical User Interface) window generated by the radiographic image processing apparatus according to the first embodiment will be described next with reference to FIG. 1B.

Figure 1B:
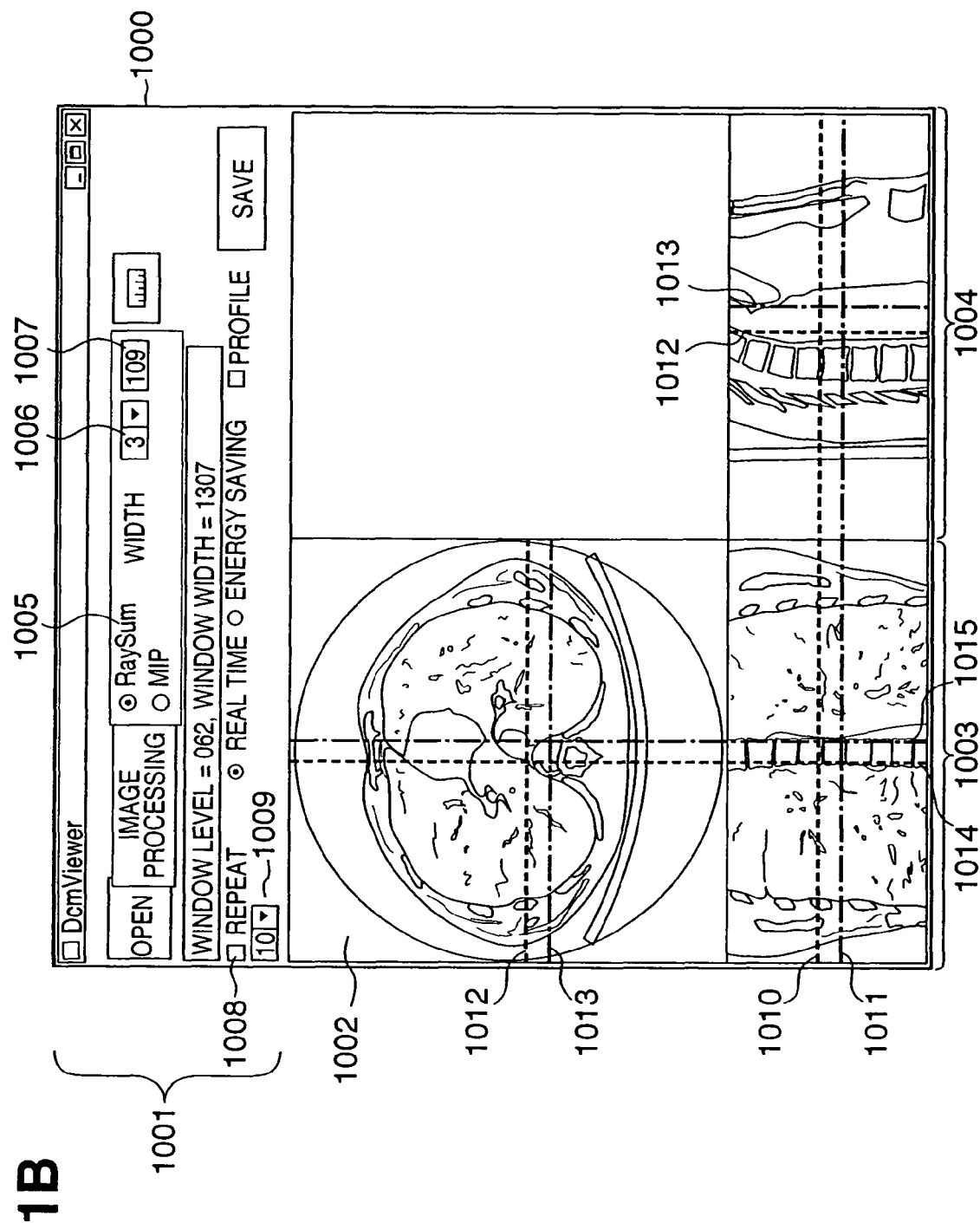
FIG. 1B is a view showing an example of a GUI window on the radiographic image processing apparatus according to the first embodiment of the present invention.

FIG. 1B is a view showing an example of the GUI window on the radiographic image processing apparatus according to the first embodiment of the present invention.

FIG. 1B shows a case wherein 300 CT images each comprising 512×512 pixels are given. The constituent pixels of a CT image each have a size of 0.7 mm square.

The file names of CT image files for the 300 CT images are partly assigned serial numbers from 000 to 299. The CT images are sequentially stored in the data storage unit 103 in accordance with the serial numbers from above to below of the imaged subject. In addition, the image cross section intervals of the subject are 0.7 mm, and hence each pixel is a 0.7-mm cube.

A display screen 1000 is divided into a control area 1001, axial image display area 1002, sagittal image display area 1003, and coronal image display area 1004.

The control area 1001 includes two tabs, namely "open" tab and "image processing" tab. The user can selectively switch these tabs by using the input unit 101 and operate the operation GUI (control) prepared for each tab.

For "Open" tab, an operation GUI associated with file operations ("open file", "save file", "close file", and the like) is mainly provided. For "image processing" tab, an operation GUI associated with image processing is provided. FIG. 1B shows a display state when "image processing" tab is selected.

Note that "open" tab allows the user to operate a plurality of files of the above consecutive CT image files and simultaneously set a pixel size and image cross section intervals. FIG. 1B shows the display result obtained when "image processing" tab is selected upon completion of the above settings.

As shown in FIG. 1C, in the first embodiment, images displayed in the axial image display area 1002, sagittal image display area 1003, and coronal image display area 1004 in FIG. 1B can be handled, and similar image processing can be performed for each of the images independently.

In the first embodiment, in particular, a plurality of slice images corresponding to a subject is regarded as voxel data (solid data), and the images are classified on the basis of an idea that a cross section image group obtained by slicing along planes perpendicular to the vertical direction of the subject is an axial image group, a cross section image group obtained by slicing along planes perpendicular to the transverse direction of the subject is a sagittal image group, and a cross section image group obtained by slicing along planes perpendicular to the anteroposterior direction of the subject is a coronal image group. These images correspond to image data. The respective processing results are then reflected in the respective image display areas.

For the sake of easy understanding, only an axial image group will be described in detail below. In this apparatus, however, similar arrangements are provided for sagittal images and coronal images.

Axial images are displayed in the axial image display area 1002. Such axial images are obtained by performing display processing for an axial image group within the range designated by a range designating unit realized on the control area 1001.

The range designating unit corresponds to a start axial image number 1007, image processing range image count 1006, and display range image count 1009 in FIG. 1B. The values (range information) designated by this range designating unit are stored in a memory in the control unit 102. A plurality of consecutive images equal to the number of images designated as a display range image count, starting from a start axial image corresponding to the designated start axial image number, fall within a display target range.

The user can change the start axial image number by, for example, moving the mouse wheel forward and backward in the axial image display area 1002.

Alternatively, the start axial image number 1007 may be formed as a numerical value input field to allow the user to change the start axial image number by directly inputting a desired start axial image number.

In addition, alternatively, the start axial image number may be changed by using a mouse wheel with a tilt function and setting the tilt function such that when the mouse wheel is tilted to the right, the start axial image number is incremented, and when the mouse wheel is tilted to the left, the start axial image number is decremented.

Any method can be used for changing the start axial image number as long as it can change it. This method includes a method using buttons, keys, and wheel of an input device including a pointing device such as a mouse or a method using an operation GUI (control: a pull-down menu, input fields, radio buttons, and check boxes) on the display screen.

The display range image count and image processing range image count can be changed by performing pull-down menu operation with respect to the display range image count 1009 and image processing range image count 1006 formed by pull-down menus so as to select a desired display range image count and a desired image processing range image count. Any method for changing the display range image count and image processing range image count can be used as long as the method can change them as in the case with the changing of the start axial image number.

Referring to FIG. 1B, an axial image start line 1010 and axial image end line 1011 indicate which portions of the sagittal image display area 1003 and coronal image display area 1004 the display range area defined by the start axial image and an image spaced apart from the start axial image by the display range image count corresponds. That is, these lines indicate the depth direction of the display target range.

When sagittal images are process targets, a start sagittal image number, image processing range image count, and display range image count on the range designating unit are set. A sagittal image start line 1012 and sagittal image end line 1013 indicate which portions of the axial image display area 1002 and coronal image display area 1004 the range area defined by the set start sagittal image and an image spaced apart from the start sagittal image by the range image count corresponds.

When coronal images are process targets, a start coronal image number, image processing range image count, and display range image count on the range designating unit are set. A coronal image start line 1014 and coronal image end line 1015 indicate which portions of the axial image display area 1002 and sagittal image display area 1003 the range area defined by the set start coronal image and an image spaced apart from the start coronal image by the range image count corresponds.

Referring to FIG. 1B, when the user turns on (checks) a repetitive display check box 1008 by operating the input unit 101, the repetitive display mode is set.

The repetitive display mode will be described with reference to FIGS. 2A and 2B.

Figure 2A:
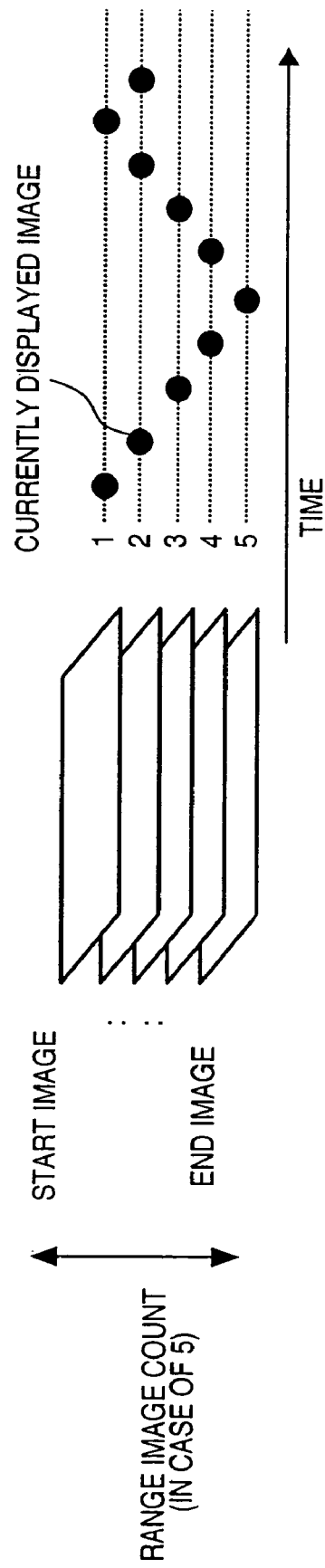
FIG. 2A is a view for explaining a bidirectional reciprocating mode in repetitive display modes according to the first embodiment of the present invention.
Figure 2B:
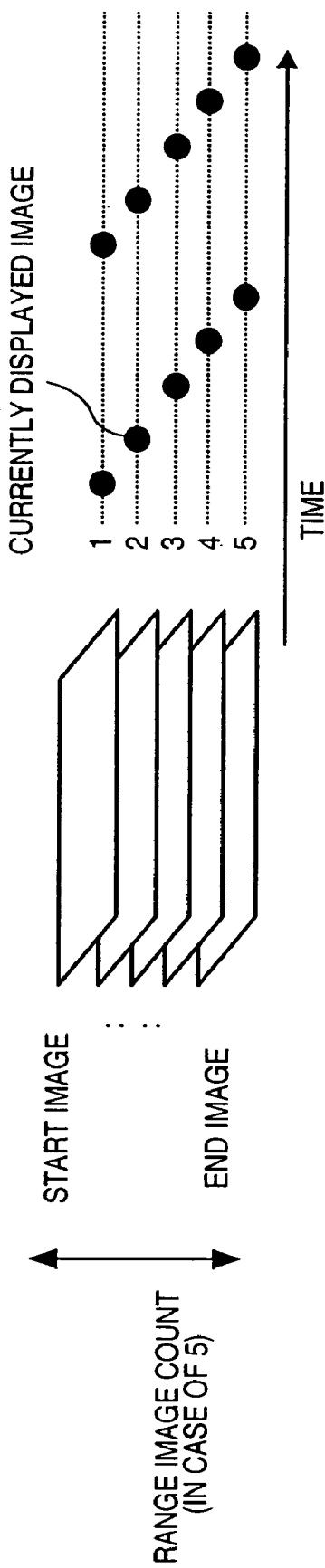
FIG. 2B is a view for explaining a unidirectional reciprocating mode in the repetitive display modes according to the first embodiment of the present invention.

FIGS. 2A and 2B are views for explaining the repetitive display mode according to the first embodiment of the present invention.

FIGS. 2A and 2B show how display processing is performed in the repetitive display mode. In the axial image display area 1002, images within the range area defined by the start axial image designated by the range designating unit and an image spaced apart from the start axial image by a range image count are sequentially switched at a high speed (e.g., 3 Hz or more) to display an image in accordance with timer events (to be described later). In this case, the range image count is "5".

For display switching by timer events, one of the following modes can be selected in advance: the bidirectional reciprocating mode (FIG. 2A) of displaying consecutive images while alternately switching the forward and backward directions like 1, 2, 3, 4, 5, 4, 3, 2, 1, 2, 3, . . . ; and the unidirectional reciprocating mode (FIG. 2B) of repetitively displaying consecutive images in the forward direction like 1, 2, 3, 4, 5, 1, 2, 3, 4, 5, 1, . . . , as shown in FIGS. 2A and 2B.

In display operation, LUT gradation processing is performed for each 12-bit pixel image of a currently displayed image to generate a display 8-bit image. In addition, this image is enlarged/reduced so as to fit in a corresponding axial image display area. This processing will be described in detail later.

Referring to FIG. 1B, assume that an image processing method is selected by an image processing type selecting unit 1005, the image processing range image count 1006 is set to a value larger than "1", and the repetitive display mode is turned on with the repetitive display check box 1008. In this case, the processed image repetitive display mode is set. Setting the image processing range image count to a value larger than "1" makes it possible to execute the repetitive display mode with image processing being performed between a plurality of images.

This processed image repetitive display mode will be described next with reference to FIG. 3.

Figure 3:
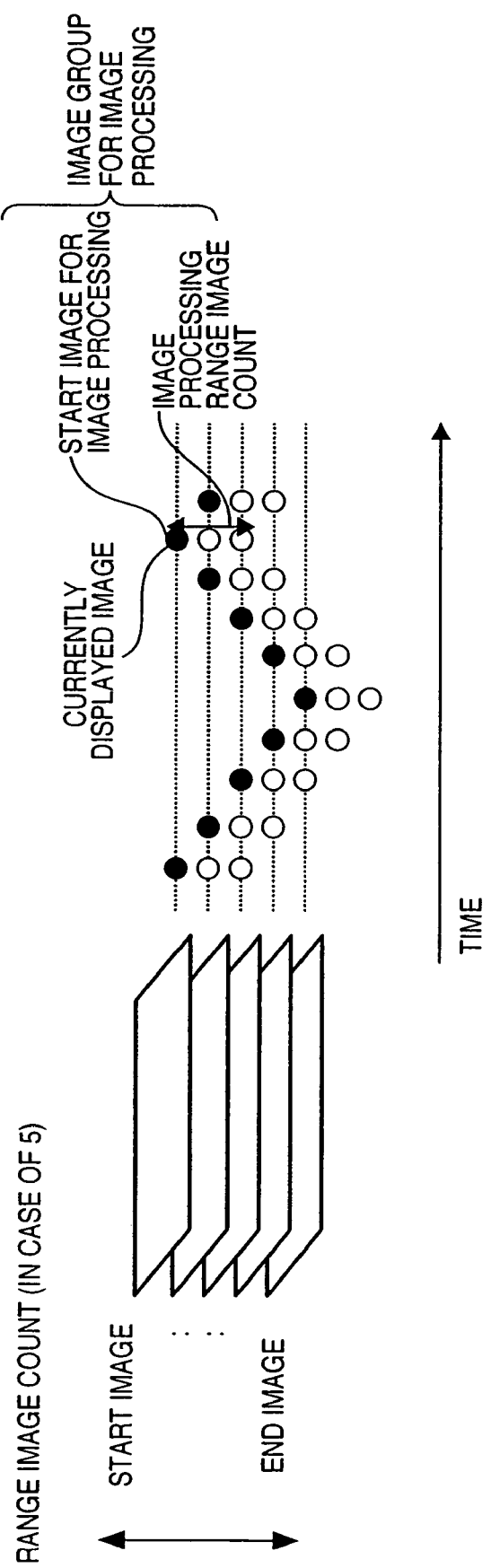
FIG. 3 is a view for explaining a process image repetitive display mode according to the first embodiment of the present invention.

FIG. 3 is a view for explaining the processed image repetitive display mode according to the first embodiment of the present invention.

FIG. 3 shows an example of the processed image repetitive display mode. On the display screen 1000 in FIG. 1B, a display range image count is set as in the case of the repetitive display mode. In this case, the RaySum radio button is selected in the image processing type selecting unit 1005 comprising radio buttons, and the image processing range image count is set to "3".

In the processed image repetitive display mode, images are switched within a range area corresponding to the range image count in the same manner as the above-described repetitive display mode, but a display image generating unit (to be described in detail later) generates each display image by performing RaySum processing using each image of the image group set by the image processing range image count. Each 12-bit pixel image of the display image having undergone RaySum processing is subjected to table processing to generate an 8-bit image for display, which in turn is enlarged/reduced to fit in a corresponding axial image display area. This processing will be described in detail later.

RaySum processing will be described with reference to FIG. 4.

Figure 4:
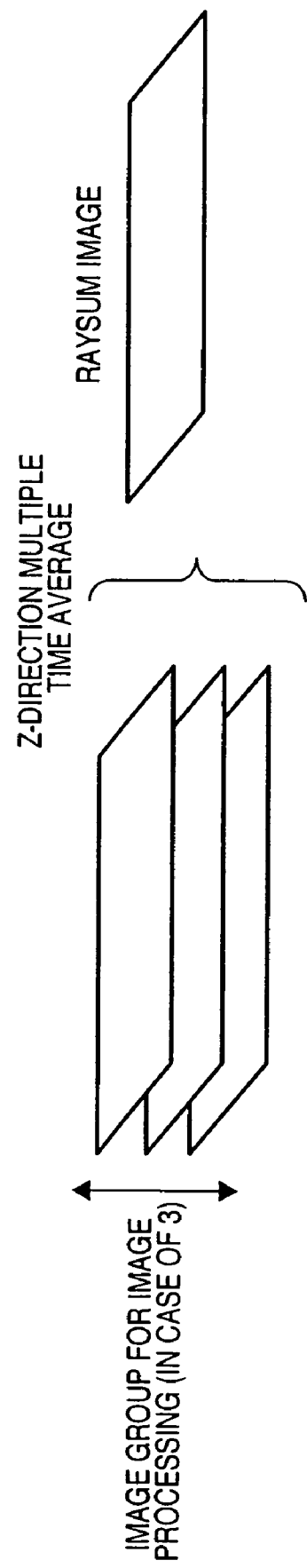
FIG. 4 is a view for explaining RaySum processing according to the first embodiment of the present invention.

FIG. 4 is a view for explaining RaySum processing according to the first embodiment of the present invention.

FIG. 4 shows an example of a RaySum processing method. In RaySum processing, averaging processing is performed for each corresponding pixel of a target image group for image processing to generate an average image (RaySum image) of consecutive images within a predetermined range.

Note that the image processing type selecting unit 1005 in FIG. 1B includes an MIP (Maximum Intensity Projection) radio button for generating an MIP image of consecutive images in a predetermined range by using a maximum pixel value in each corresponding pixel in a target image group for image processing, in addition to the RaySum radio button. In addition to these radio buttons, an image processing radio button for applying arbitrary image processing to a target image group for image processing can be added to the image processing type selecting unit 1005, as needed, by adding an add-on library thereto.

The functional arrangement of the radiographic image processing apparatus according to the first embodiment will be described next with reference to FIG. 5.

Figure 5:
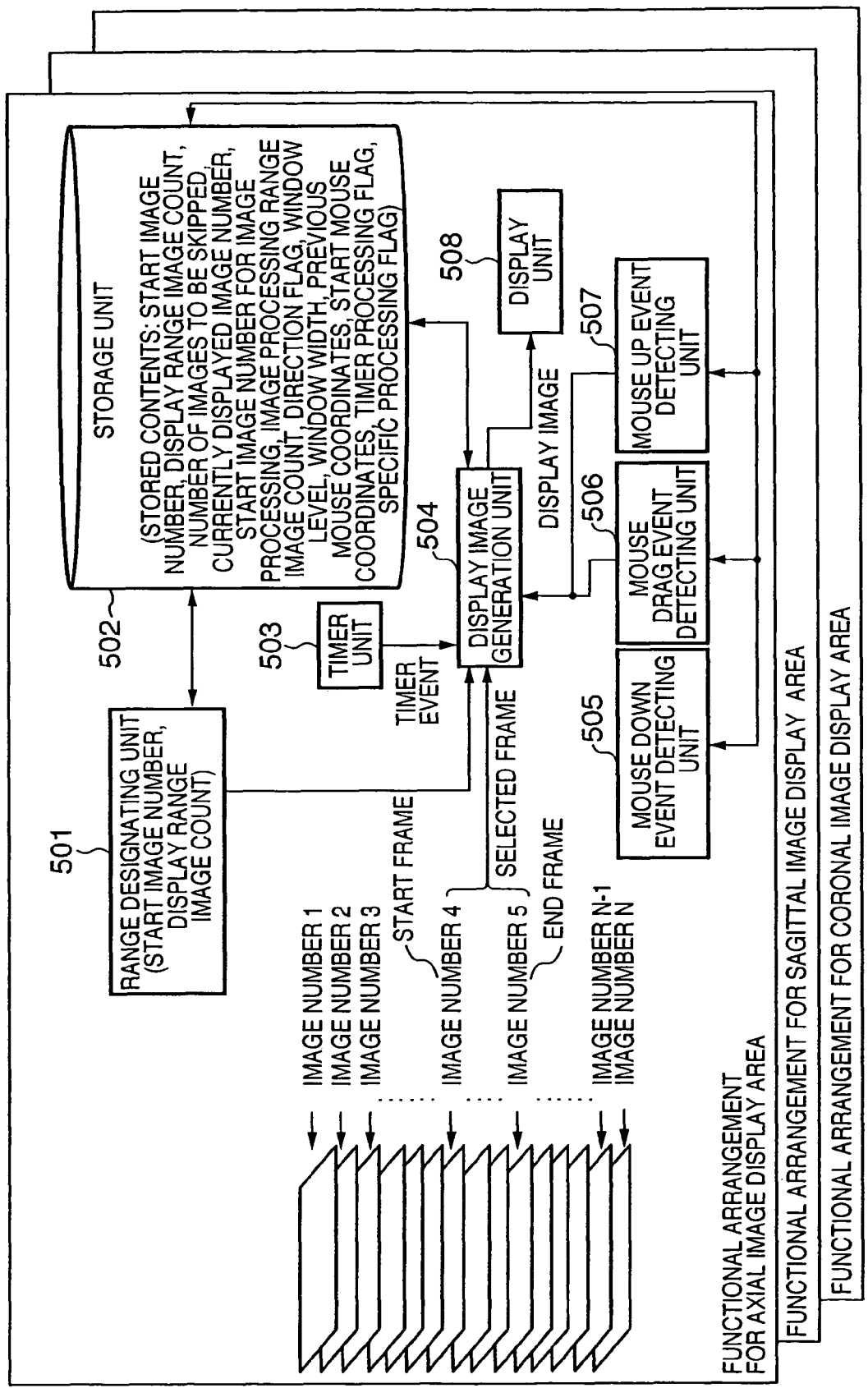
FIG. 5 is a view showing the functional arrangement of the radiographic image processing apparatus according to the first embodiment of the present invention.

FIG. 5 shows the functional arrangement of the radiographic image processing apparatus according to the first embodiment of the present invention. The functional arrangement shown in FIG. 5 exemplifies only the functional arrangement of the axial image display area 1002. This apparatus, however, has similar functional arrangements for the sagittal image display area 1003 and coronal image display area 1004.

By using a range designating unit 501, the user designates a start axial image with the mouse wheel and designates a display range image count and image processing range image count by GUI operation. Assume that the start axial image number is to be changed by the mouse wheel. In this case, rotating the mouse wheel forward increments the start axial image number by the number of images to be skipped which corresponds to the rotation amount of the mouse wheel. Rotating the mouse wheel backward decrements the start axial image number by the number of images to be skipped which corresponds to the rotation amount.

These values are stored/managed in a storage unit 502 realized by the data storage unit 103. The number of images to be skipped is a value for setting how many the start axial image number is changed by rotating the mouse wheel by one division. The initial value of the number of images to be skipped is set to be equal to the display range image count. Although a value different from the display range image count can be set to the number of images to be skipped, any value exceeding the display range image count cannot be set.

Operations associated with mouse clicking and dragging are detected by a mouse down event detecting unit 505, mouse drag event detecting unit 506, and mouse up event detecting unit 507.

In this embodiment, a mouse is used as the input unit 101. The dragging operation of the mouse means a series of operations of performing mouse button down operation (mouse down: indicating the start of dragging operation), moving the mouse from the position where the mouse button is pressed down to an arbitrary position while holding the mouse in the "down" state, and releasing the mouse button (mouse up: indicating the end of dragging operation).

This dragging operation can be realized by an input device other than the mouse.

For example, an input pen having a switch such as a pen-point switch or pen-side switch may be used as the input unit 101. In this case, when dragging operation is performed with the input pen, dragging operation also corresponds, for example, to a series of operations of turning on the pen-point switch (pen down), moving the pen from the position where the switch is turned on to an arbitrary position while the pen is held in the ON state, and turning off the pen-point switch (pen up).

As the input unit 101, a touch panel may be used. In this case, when dragging operation is performed with the touch panel, dragging operation corresponds to a series of operations of touching the touch panel with an indicating tool such as a finger (touch-down operation), moving the indicating device from the position where the touch panel is touched to an arbitrary position while the indicating device is held in the touched state, and releasing the indicating device (touch-up operation).

A timer processing flag (a flag indicating the presence/absence of a timer event) is a flag for controlling whether to generate a timer event by using the timer unit 503. When the mouse down event detecting unit 505 detects an event in the axial image display area 1002 on the display screen 1000, the timer processing flag in the axial image display area is turned on. When the mouse down event detecting unit 505 detects an event in the sagittal image display area 1003 or coronal image display area 1004 which is an image display area other than the axial image display area 1002 on the display screen 1000, the timer processing flag in the axial image display area is turned off.

Likewise, when the mouse down event detecting unit 505 detects an event in the sagittal image display area 1003, the timer processing flag in the sagittal image display area is turned on. When the mouse down event detecting unit 505 detects an event in the axial image display area 1002 or coronal image display area 1004 which is an image display area other than the sagittal image display area 1003, the timer processing flag in the sagittal image display area is turned off.

In addition, when the mouse down event detecting unit 505 detects an event in the coronal image display area 1004, the timer processing flag in the coronal image is turned on. When the mouse down event detecting unit 505 detects an event in the axial image display area 1002 or sagittal image display area 1003 which is an image display area other than the coronal image display area 1004, the timer processing flag in the coronal image is turned off.

In any case, when a mouse down event occurs at a position other than the image display area on the display screen 1000, the occurrence of a mouse down event is neglected, and ON/OFF control is not performed for the timer processing flag.

In this manner, the user can visually check how display image generation (switching) processing is performed for an image in the image display area at the mouse down position by a timer event by the timer unit 503 upon occurrence of the mouse down event, and the display is changed.

A display image generation unit 504 generates a display image in only cross section image display area where the timer processing flag is ON, in accordance with a window level and window width (to be described later). At this time, when a mouse down event occurs in another cross section image display area, the timer processing flag in the cross section image display area is turned off, and display image generation processing is stopped.

Note that processing in the range designating unit 501, timer unit 503, mouse down event detecting unit 505, mouse drag event detecting unit 506, and mouse up event detecting unit 507 is exclusively controlled. For this reason, the range designating unit 501 and timer unit 503 do not operate simultaneously, and the consistency of the memory in the storage unit 502 is always maintained.

Processing in the range designating unit 501 will be described with reference to FIG. 6.

Figure 6:
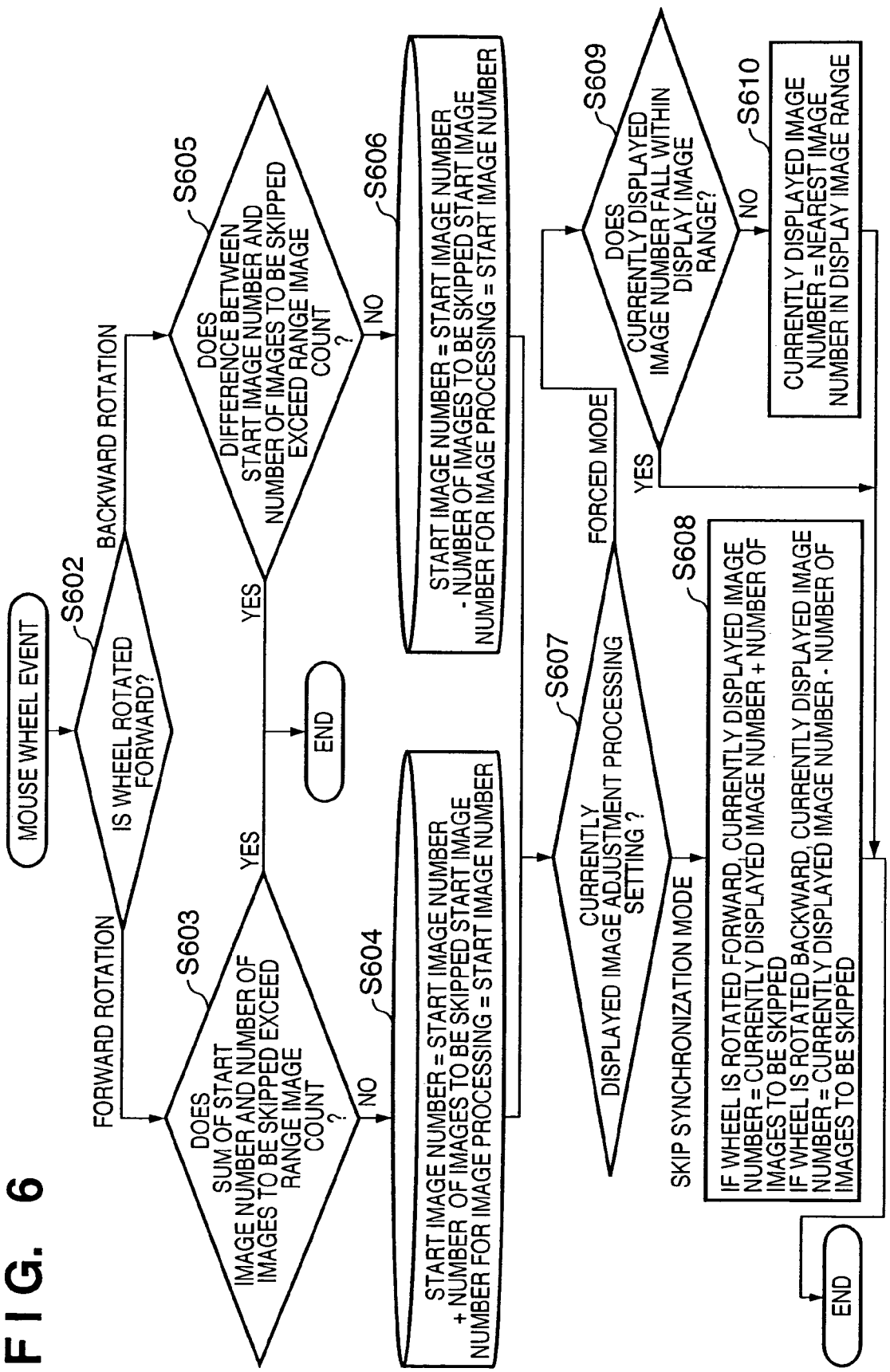
FIG. 6 is a flowchart showing processing in a range designating unit according to the first embodiment of the present invention.

FIG. 6 is a flowchart showing processing in the range designating unit according to the first embodiment of the present invention.

When the user issues an instruction to change the start axial image number with the mouse wheel on the display screen 1000, a mouse wheel event occurs. First of all, it is determined whether the rotating direction of the mouse wheel is the forward rotating direction (step S602). If the rotating direction of the wheel is the forward rotating direction, it is determined whether the image number obtained by adding the number of images to be skipped to the start image number exceeds the maximum image number of an image which can be displayed (step S603). If the image number exceeds the maximum number of the image which can be displayed (YES in step S603), the processing is terminated. In this case, the displayed image on the display screen 1000 is not changed.

If the image number obtained by adding the number of images to be skipped to the start image number falls within the maximum image number of the image which can be displayed (NO in step S603), the image number obtained by adding the number of images to be skipped to the current start image number is set as a new start image number, and the contents of the storage unit 502 are updated. In the first embodiment, since the start image number for image processing which is a start point of image processing targets is the same as the start image number as a start point of display, a start image is set for images subjected to image processing (step S604). Even if the start image number for image processing differs from the start image number for display, the gist of the present invention is not impaired.

If it is determined in step S602 that the rotating direction of the wheel is the backward rotating direction (inverting direction), it is determined whether the image number obtained by subtracting the number of images to be skipped from the start image number exceeds the minimum image number of an image which can be displayed (step S605). If the image number exceeds the minimum image number of the image which can be displayed (YES in step S605), the processing is terminated. In this case, the displayed image on the display screen 1000 is not changed.

If the image number obtained by subtracting the number of images to be skipped from the start image number falls within the minimum image number of the image which can be displayed (NO in step S605), the image number obtained by subtracting the number of images to be skipped from the current start image number is set as a new start image number, and the contents of the storage unit 502 are updated. In the first embodiment, since the start image number for image processing which is a start point of image processing targets is the same as the start image number as a start point of display, the start image number is set to the image number for image processing (step S606).

The processing in step S603 or S605 is performed such that the change of the display image range (range information) indicated by the start image number and display range image count changed with mouse wheel operation is so controlled as to make images consecutive with respect to the display image range (range information) indicated by the start image number and display range image count stored in the storage unit 502 before the change. This operation is performed to prevent the loss of the continuity of images between the display image range before the change and the display image range after the change.

That is, this operation is performed to prevent the generation of an image which does not belong to either of the display image ranges before and after the change. More specifically, if an image which does not belong to either of the display image range before the change and the display image rage after the change is generated between them, the image which does not belong to either of the display image ranges is forcibly displayed, and the display image range after the change is changed.

The start image changing processing in step S604 or S605 is set in either of two modes, i.e., a skip synchronization mode and a forced mode, by system setting called adjusting processing setting for a currently (or target) displayed image (step S607). If display image adjustment processing setting is set in the skip synchronization mode, when the start image number is changed, the currently displayed image number in the storage unit 502 is changed by the number of images to be skipped (step S608). For this reason, when a timer event is generated by the timer unit 503, the change of the display image range is properly processed to perform image transition in a more natural manner.

In step S608, display switching by mouse wheel operation for the currently displayed image is executed following mouse wheel operation. In this case, when the mouse wheel is continuously rotated at a high speed, switching of the currently displayed image may not follow the rotating operation depending on the rotational speed. That is, if the switching speed of the currently displayed image cannot catch up with the rotational speed of the mouse wheel, the next currently displayed image may be displayed after some of the images between the currently displayed image and the next currently displayed image corresponding to the rotation amount are skipped.

Such an arrangement, however, is not preferable for diagnosis because consecutive images cannot be observed. In this embodiment, therefore, when mouse wheel operation is done such that the switching speed of the currently displayed image cannot catch up with the rotational speed of the mouse wheel, the following processing is executed. That is, the rotation amount at the end of rotation is stored in the storage unit 502. When switching of the currently displayed image is to be performed in accordance with the rotation amount, the currently displayed image is switched after the images between the currently displayed image and the currently displayed image after switching are forcibly displayed so as to maintain the continuity of the currently displayed images to be switched.

If it is determined in step S607 that currently displayed image adjustment processing setting is to be performed in the forced mode, it is checked whether the currently displayed image number stored in the storage unit 502 exists in the display image range indicated by the start image number and display range image count (step S609). If the above image number falls within the display image range (YES in step S609), the processing is terminated. If the image number falls outside the display image range (NO in step S609), an image of an image number nearest to the currently displayed image number within the display image range is corrected/changed to the currently displayed image (step S610).

In this case, the timer unit 503 in FIG. 5 generates timer events at predetermined time intervals. Upon receiving a timer event from the timer unit 503, the display image generation unit 504 reads in an image data group (image group) corresponding to the display range image count, and generates display images. Alternatively, upon receiving an instruction from the range designating unit 501, the display image generation unit 504 reads in an image data group (image group) corresponding to the display range image count, and generates display images. The generated display images are displayed by a display unit 508.

The timer unit 503 executes a timer event when the timer processing flag stored in the storage unit 502 is ON. This flag is turned on when a mouse down event is detected by the mouse down event detecting unit 505. This will be described later.

Processing in the display image generation unit 504 will be described next with reference to FIG. 7.

Figure 7:
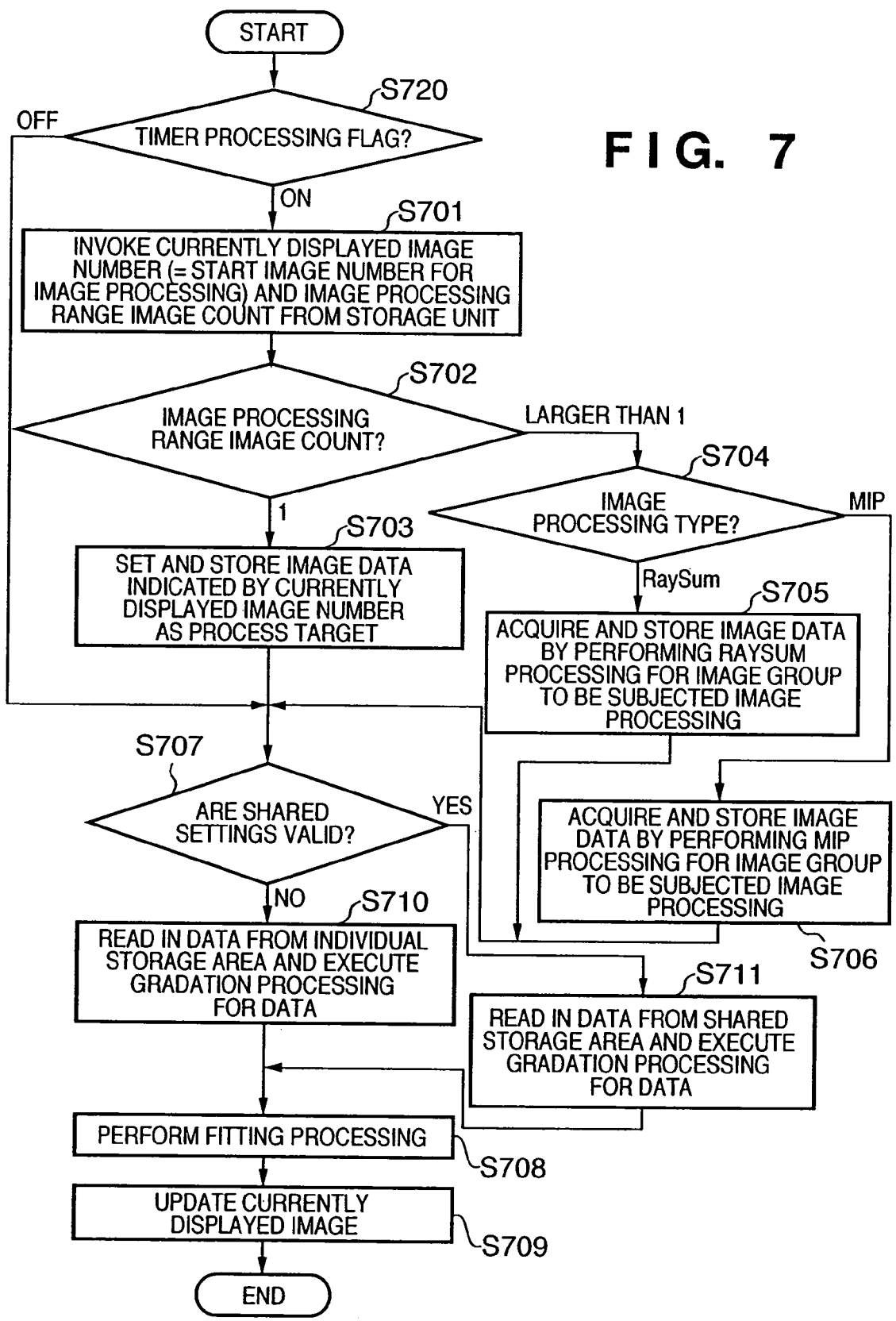
FIG. 7 is a flowchart showing processing in a display image generating unit according to the first embodiment of the present invention.

FIG. 7 is a flowchart showing processing in the display image generating unit according to the first embodiment of the present invention.

First of all, the status of the timer processing flag is checked (step S720). If the timer processing flag is OFF, it is determined by referring to the system settings whether the shared settings of a window level and window width are valid (step S707).

If the shared settings are valid (YES in step S707), the image processing parameters of the window level and window width stored in a shared storage area in the storage unit 502 are read out. At this point of time, gradation processing based on the window level and window width is executed for the image data stored in the storage unit 502 (step S711).

If the shared settings are invalid (NO in step S707), the image processing parameters of the window level and window width stored in individual storage area in the storage unit 502 are read out. At this point of time, gradation processing based on the window level and window width is executed for the image data stored in the storage unit 502 (step S710).

If it is determined in step S720 that the timer processing flag is ON, the flow advances to the processing in step S701 and subsequent steps.

First of all, the currently displayed image number (which is identical to the start image number for image processing in the first embodiment) and the image processing range image count are invoked from the storage unit 502 (step S701). Note that in the first embodiment, since the currently displayed image number is identical to the start image number for image processing, it suffices to invoke only one of the above numbers.

It is then determined whether the image processing range image count is larger than "1" (step S702). If the image processing range image count is equal to "1", image data indicated by the currently displayed image number is set as a process target and is stored in the storage unit 502 (step S703).

Setting the image processing range image count to a value larger than "1" validates image processing between a plurality of images. In addition, as shown in FIG. 3, images which consecutively follow the currently displayed image number and fall within the range of the image processing range image count become image process targets (an image group for image processing).

If it is determined in step S702 that the image processing range image count is larger than "1", the type of inter-image image processing is determined (step S704). This determination is executed on the basis of the acquired radio button value of the image processing type selecting unit 1005 on the display screen 1000.

If the RaySum radio button is selected, RaySum processing is performed for images for image processing which successively follow the currently displayed image number by the image processing range image count. Image data as display images are acquired on the basis of the processing result, and are stored in the storage unit 502 (step S705).

When the MIP radio button is selected, MIP processing is performed for images for image processing which successively follow the currently displayed image number by the image processing range image count. Image data representing display images are acquired on the basis of the processing result, and are stored in the storage unit 502 (step S706).

It is determined by referring to the system settings whether the shared settings of a window level and window width are valid (step S707).

If the shared settings are valid (YES in step S707), the image processing parameters of the window level and window width stored in the shared storage area in the storage unit 502 are read out. Gradation processing based on the window level and window width is then executed for the image data stored in the storage unit 502 by using the readout image processing parameters (step S711).

If the shared settings are invalid (NO in step S707), the image processing parameters of the window level and window width stored in the individual storage area in the storage unit 502 are read out. Gradation processing based on the window level and window width is then executed for the image data stored in the storage unit 502 by using the readout image processing parameters (step S710).

Figure 8:
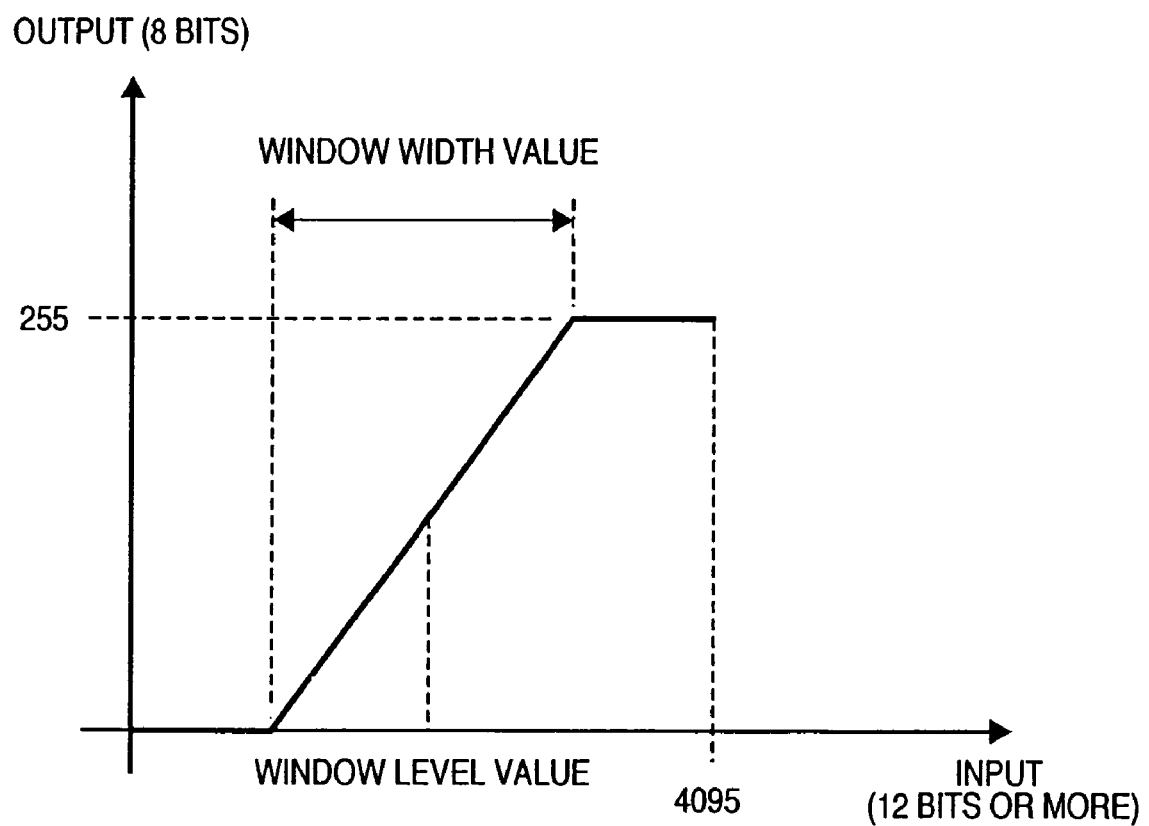
FIG. 8 is a graph for explaining a window level and window width according to the first embodiment of the present invention.

In this case, as shown in FIG. 8, window levels (processing contrast heights) and window widths (processing contrast widths) are image processing parameters which confirm an input/output linear table, which is often used in the medical image industry.

Subsequently, fitting processing of enlarging/reducing image data as a process target is executed in accordance with an image display area (step S708). With this processing, the generation of image display data with respect to the image display area is complete. Thereafter, the currently displayed image is updated (step S709).

As shown in FIGS. 2A and 2B as well, the currently displayed image is updated in either the bidirectional reciprocating mode or the unidirectional reciprocating mode. In the bidirectional reciprocating mode, if the currently displayed image number is the image number at the end point of the display image range, the currently displayed image is updated in the backward direction. In the bidirectional reciprocating mode, a direction flag is stored in the storage unit 502, and the updating direction of an image is controlled.

On the other hand, in the unidirectional reciprocating mode, if the currently displayed image number at an end of the display image range is the image number at the end point of the display image range, the currently displayed image is updated to the image at the start point of the display image range.

As described above, the currently displayed image is updated in accordance with these modes.

Processing in each of the mouse down event detecting unit 505, mouse drag event detecting unit 506, and mouse up event detecting unit 507 will be described next with reference to FIGS. 9 to 11. These three event detecting units function exclusively for the axial image display area, and three event detecting units are prepared for each of the coronal image display area and sagittal image display area.

In this case, if the mouse position is detected by the operating system or the like, and the mouse position is in the axial image display area, the position is notified to the event detecting unit for the axial image display area. Likewise, if the mouse position in the coronal image display area, the position is notified to the event detecting unit for the coronal image display area. If the mouse position is in the sagittal image display area, the position is notified to the event detecting unit for the sagittal image display area.

Processing in the mouse down event detecting unit 505 will be described with reference to FIG. 9.

Figure 9:
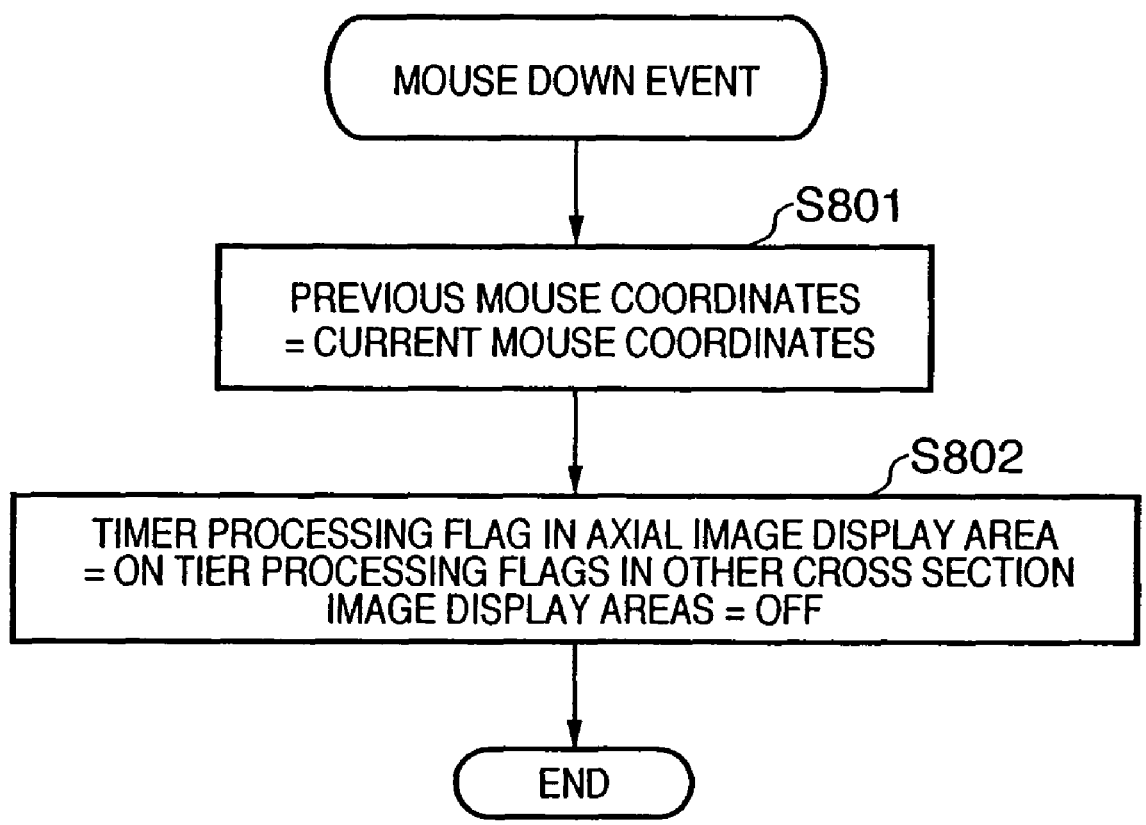
FIG. 9 is a flowchart showing processing in a mouse down event detecting unit according to the first embodiment of the present invention.

FIG. 9 is a flowchart showing processing in the mouse down event detecting unit in the axial image display area according to the first embodiment.

Note that this mouse down event is a process event for a shift to the display image generation processing mode (specific processing mode) by the display image generation unit 504.

The previous mouse coordinates in the storage unit 502 are set as current mouse coordinates (step S801). The timer processing flag in the axial image display area is turned on, and the timer processing flags in the coronal image display area and sagittal image display area, which are image display areas other than the axial image display area, are turned off (step S802).

Processing in the mouse drag event detecting unit 506 will be described next with reference to FIG. 10.

Figure 10:
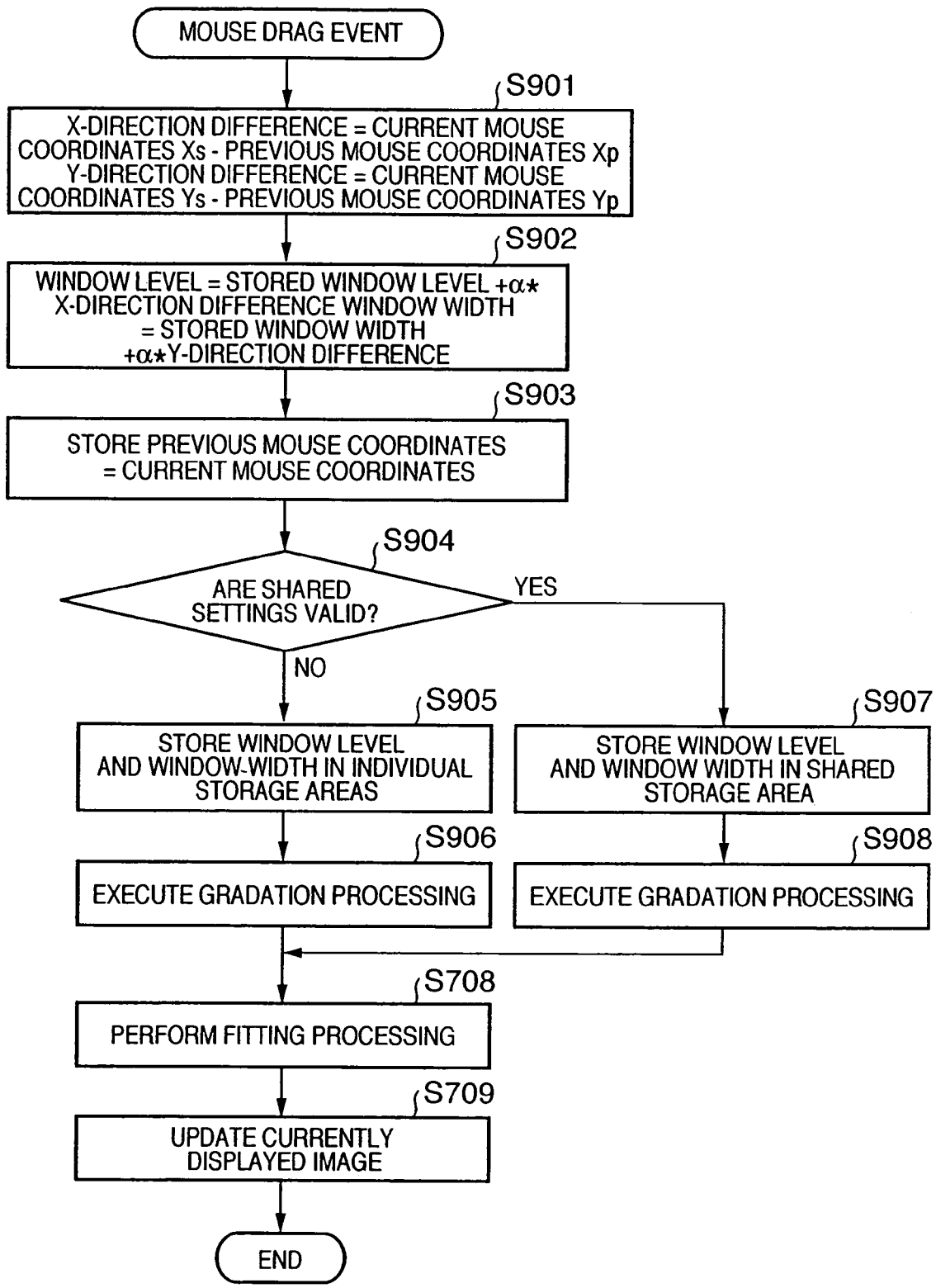
FIG. 10 is a flowchart showing processing in a mouse drag event detecting unit according to the first embodiment of the present invention.

FIG. 10 is a flowchart showing processing in the mouse drag event detecting unit in the axial image display area according to the first embodiment.

Note that since this mouse drag event occurs every time the mouse drag amount changes upon mouse operation, a mouse drag event does not necessarily occur once. That is, a mouse drag event is a change event that occurs when the mouse drag amount changes.

When a mouse drag is detected, a mouse drag event processing step is executed. First of all, mouse operating direction differences (an X-direction difference and Y-direction difference) are calculated by using the differences between the previous mouse coordinates (Xp, Yp) stored in the storage unit 502 and the current mouse coordinates (Xs, Ys) (step S901).

Subsequently, the products (variations equivalent to change amounts) of the X- and Y-direction differences and a predetermined magnification a are added to the window level and window width stored in the storage unit 502 to calculate new window level and window width (step S902). The previous mouse coordinates stored in the storage unit 502 are updated as the current mouse coordinates (step S903).

It is then determined by referring to the system settings whether the shared settings of the window level and window width are valid (step S904). If the shared settings are invalid (NO in step S904), the image processing parameters of the window level and window width are stored in the individual storage area in the storage unit 502 (step S905).

Subsequently, gradation processing based on the window level and window width is executed for the image data displayed in the axial image display area by using the image processing parameters of the window level and window width stored in the individual storage area in the storage unit 502 (step S906).

If it is determined in step S904 that the shared settings are valid (YES in step S904), the image processing parameters of the window level and window width are stored in the shared storage area in the storage unit 502 (step S907).

Gradation processing based on the window level and window width is then executed for the image data displayed in all the cross section image display areas by using the image processing parameters of the window level and window width stored in the shared storage area in the storage unit 502 (step S908).

Subsequently, the processing in steps S708 and S709 in the flowchart of FIG. 7 is executed.

The axial image display area 1002 has been exemplified above. In the first embodiment, however, the axial image display area 1002, sagittal image display area 1003, and coronal image display area 1004 in which images are displayed exist on the display screen 1000. Each display area independently has a functional arrangement similar to that shown in FIG. 5, and similar processing is performed.

Note, however, that the shared storage area in the storage unit 502 for the axial image display area 1002 is shared by the storage unit for the sagittal image display area 1003 and the storage unit for the coronal image display area 1004. Therefore, the window level and window width stored in this shared storage area can be shared by the storage units for the sagittal image display area 1003 and coronal image display area 1004.

If shared-settings are made by system settings, images using the window level and window width common to all the display areas, i.e., the axial image display area 1002, sagittal image display area 1003, and coronal image display area 1004, are processed and displayed. When the operator compares the respective image display areas with the eye, he/she can easily perform diagnosis by comparison between images in the respective display areas.

As described above, according to the first embodiment, even when a large number of diagnosis images are to be processed, the contents of each target diagnosis image can be easily made to be visually checked with a small number of operation steps. Since differences between images can be displayed by afterimage reduction, an image display system suitable for diagnosis can be realized.

Second Embodiment

The first embodiment is directed to a CT image file comprising a plurality of CT images. Even if, however, the present invention is applied to a moving image file indicating temporal changes, similar effects can be obtained. In this case, the axial image display area 1002 becomes a temporal image display area, and the sagittal image display area 1003 and coronal image display area 1004 become display areas indicating temporal changes along the corresponding lines.

Third Embodiment

FIG. 7 in the first embodiment shows the arrangement in which display control of images in the axial image display area 1002 is executed in accordance with the status of the timer processing flag. However, the present invention is not limited to this. Shifting to the processing in step S701 and the subsequent steps regardless of the status of the timer processing flag makes it possible to generate consecutive images to be repeatedly displayed in predetermined ranges in all the cross section image display areas. Alternatively, consecutive images to be repeatedly displayed in a predetermined range in at least one of all the cross section image display areas can be generated in accordance with the application or purpose.

In addition, cross section images obtained from solid data are not limited to axial, sagittal, and coronal images as in the first embodiment. The present invention can also be applied to three cross section images in arbitrary orthogonal directions crossing solid data.

Fourth Embodiment

The first embodiment is configured such that after a mouse down event occurs, window levels and window widths derived from the differences between the previous mouse coordinates and the current mouse coordinates are sequentially calculated in accordance with changes in mouse drag amount, and display images are generated by using the image processing parameters.

In contrast to this, the arrangement of the fourth embodiment will be described below, in which window levels and window widths derived from the differences between the current mouse coordinates and the start mouse coordinates which are the mouse down start position upon the occurrence of a mouse down event are sequentially calculated as image processing parameters, and display images are generated by using the image processing parameters.

The functional arrangement of a radiographic image processing apparatus according to the fourth embodiment is similar to that of the radiographic image processing apparatus according to the first embodiment shown in FIG. 5. FIG. 5 is a view for explaining only the functional arrangement of an axial image display area 1002. This apparatus has similar functional arrangements for a sagittal image display area 1003 and coronal image display area 1004.

More specifically, during a mouse drag event after a mouse down event, a window level and window width derived from the differences between the start mouse coordinates and the current mouse coordinates are sequentially updated and stored as first image processing parameters in a storage unit 502.

When a mouse up event occurs after a mouse drag event, a window level and window width derived from the differences between the start mouse coordinates and the current mouse coordinates are stored as first image processing parameters in the storage unit 502. In addition, the first image processing parameters are stored as second image processing parameters in the storage unit 502. The first and second image processing parameters are respectively stored in the first and second storage areas in the storage unit 502.

The first image processing parameters are derived from the differences between the start mouse coordinates and the current mouse coordinates every time a mouse drag event occurs. For this reason, the first image processing parameters become image processing parameters in which changes in mouse drag amount during mouse dragging operation are sequentially reflected. In contrast to this, the second image processing parameters become image processing parameters in which the total mouse drag amount from the start of mouse dragging operation to the end of the operation is reflected.

In the fourth embodiment, the first image display mode can be realized, in which display images are sequentially generated and updated by using the first image processing parameters in accordance with changes in mouse drag amount, and the second image display mode can be realized, in which display images can be generated and updated by using the second image processing parameters in accordance with the total mouse drag amount.

In addition, the first and second image display modes are switched by turning on/off the specific processing flags.

In the fourth embodiment, the first storage individually used for each cross section image display area is ensured in the storage unit 502, and the first image processing parameters are stored in the first storage area. With this operation, display control of each cross section image display area is performed in the first image display mode in synchronism with mouse operation, in real time, performed in a corresponding one of the cross section image display areas.

In addition, the second storage area shared by the respective cross section image display areas is ensured in the storage unit 502, and the second image processing parameters are stored in the second storage area. At the time of the end of mouse operation in any one of the cross section image display areas, display control of all the cross section image display areas including the above cross section image display area is performed in the second image display mode.

The fourth embodiment is configured to calculate the first image processing parameters on the basis of the differences between the start mouse coordinates and the current mouse coordinates. However, the present invention is not limited to this. For example, as in the first embodiment, the first image processing parameters may be calculated on the basis of the differences between the previous mouse coordinates and the current mouse coordinates.

The characteristic processing of the fourth embodiment will be described below.

Processing in a display image generation unit 504 will be described first with reference to FIG. 11.

Figure 11:
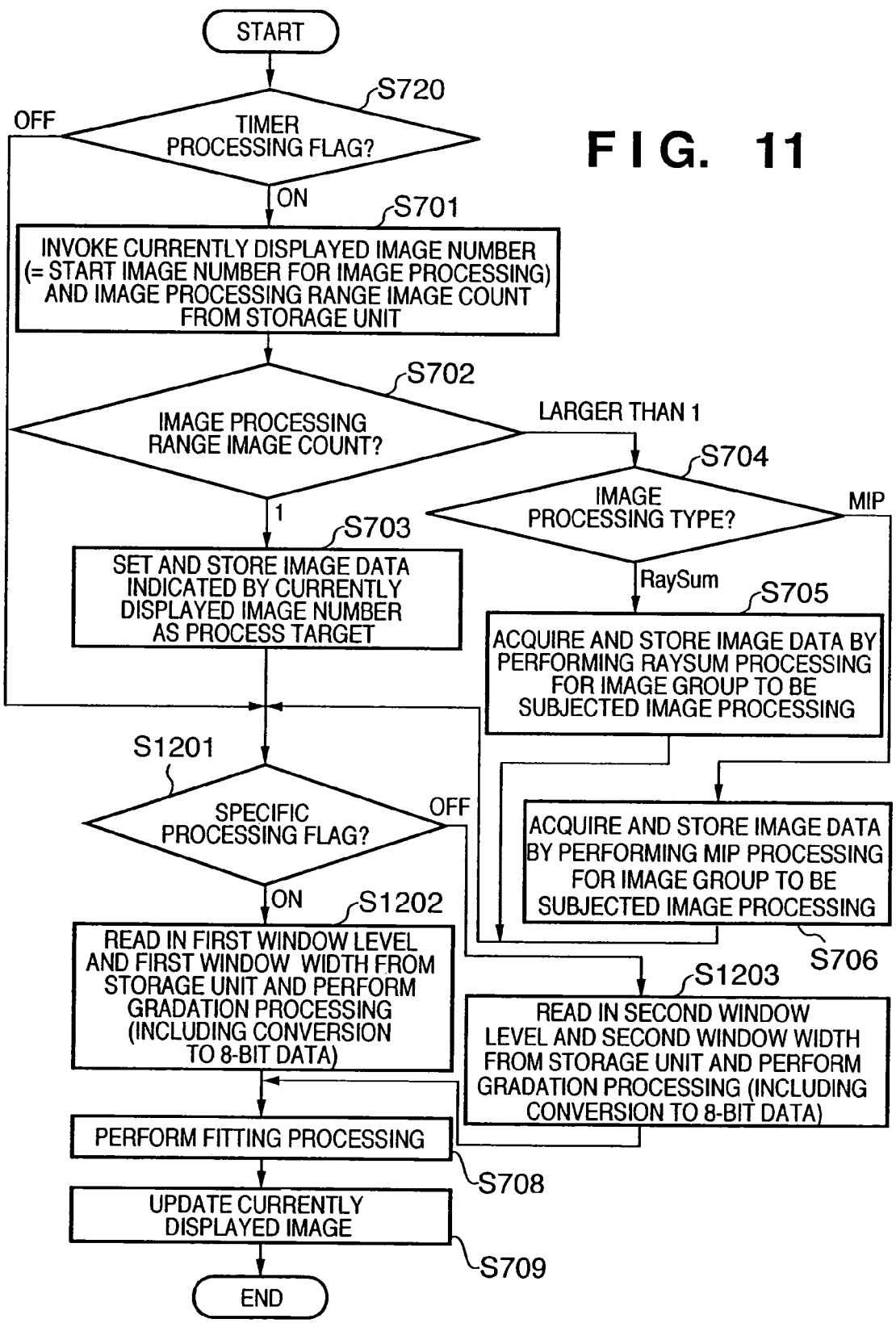
FIG. 11 is a flowchart showing processing in a display image generating unit according to the fourth embodiment of the present invention.

FIG. 11 is a flowchart showing processing in the display image generating unit in the axial image display area according to the fourth embodiment.

The same step numbers as in FIG. 7 in the first embodiment denote the same processes in FIG. 11, and a detailed description thereof will be omitted.

In the fourth embodiment, after the processing in steps S703 to S706, the status of a specific processing flag is checked. If the specific processing flag is ON, the first image processing parameters (the first window level and first window width) stored in the first storage area in the storage unit 502 are read in. By using the first image processing parameters, gradation processing is executed for the image data displayed in the cross section image display area in which the specific processing flag is ON (step S1202).

If the specific processing flag is OFF, the second image processing parameters (the second window level and second window width) stored in the second storage area in the storage unit 502 are read in. Gradation processing is then executed for the image data displayed in all the cross section image display areas by using the second image processing parameters (step S1203).

Subsequently, the processing in step S708 is executed for the image data obtained in step S1202 or S1203.

Processing in a mouse down event detecting unit 505 will be described next with reference to FIG. 12.

Figure 12:
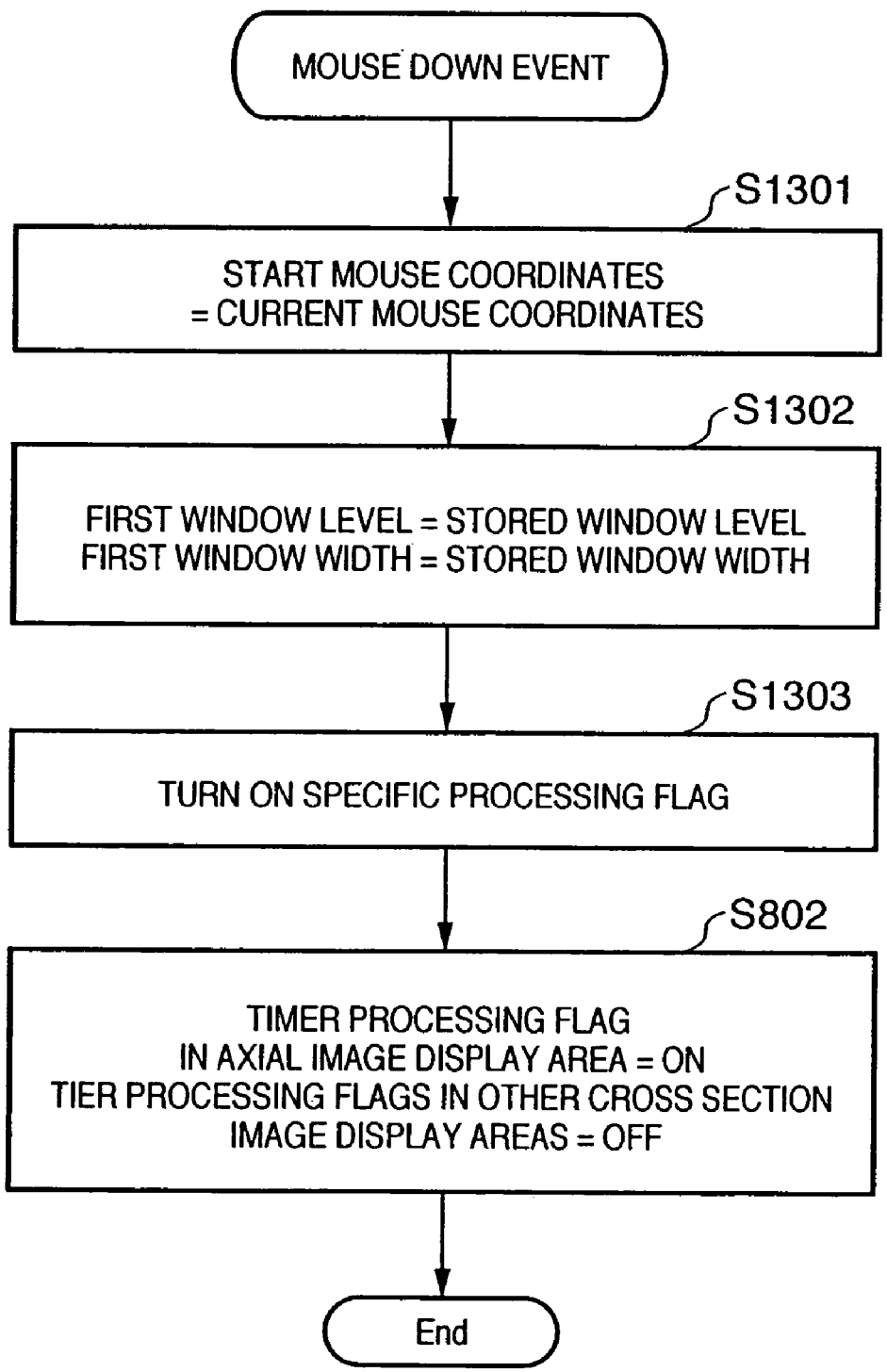
FIG. 12 is a flowchart showing processing in a mouse down event detecting unit according to the fourth embodiment of the present invention.

FIG. 12 is a flowchart showing processing in the mouse down event detecting unit 505 in the axial image display area according to the fourth embodiment.

The same step numbers as in FIG. 9 in the first embodiment denote the same processes in FIG. 12, and a detailed description thereof will be omitted.

In the fourth embodiment, the current mouse coordinates are set as start mouse coordinates (step S1301). The start mouse coordinates are stored in the storage unit 502.

The window level and window width stored in the storage unit 502 are set as first image processing parameters (a first window level and first window width) (step S1302). The specific processing flag for the axial image display area is turned on (step S1303).

With this operation, the first image processing parameters are stored in the first storage area in the storage unit 502.

Processing in a mouse drag event detecting unit 506 will be described next with reference to FIG. 13.

Figure 13:
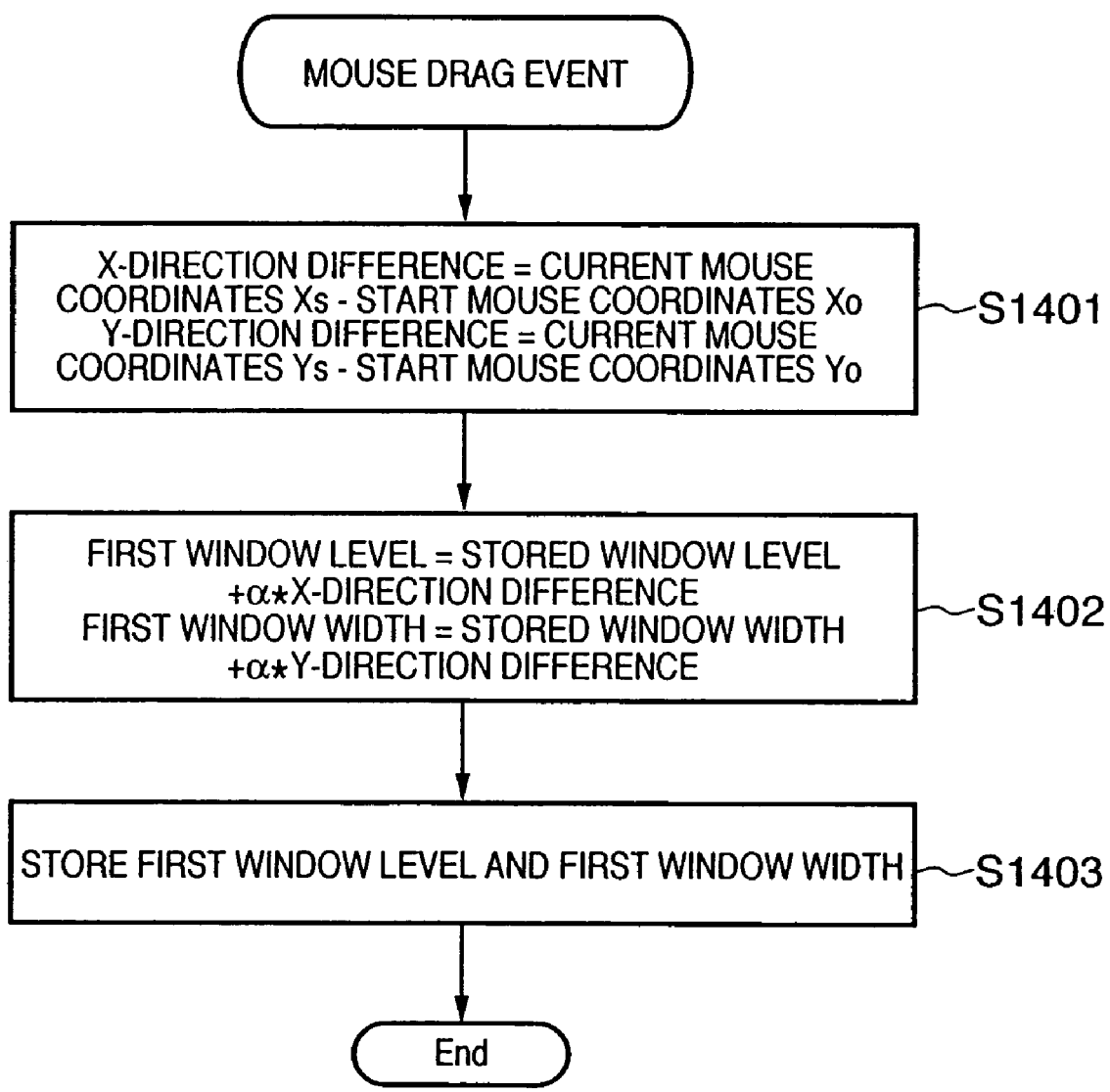
FIG. 13 is a flowchart showing processing in a mouse drag event detecting unit according to the fourth embodiment of the present invention.

FIG. 13 is a flowchart showing processing in the mouse drag event detecting unit 506 in the axial image display area according to the fourth embodiment.

When mouse dragging is detected, a mouse drag event processing step is executed. First of all, mouse operating direction differences (X- and Y-direction differences) are calculated by using the differences between the current mouse coordinates (Xs, Ys) and the start mouse coordinates (Xo, Yo) stored in the storage unit 502 (step S1401).

Subsequently, the products (variations equivalent to change amounts) of the X- and Y-direction differences and a predetermined magnification a are added to the window level and window width stored in the storage unit 502 to calculate first image processing parameters (a first window level and window width) (step S1402). The calculated first image processing parameters (the first window level and first window width) are then stored in the first storage area in the storage unit 502 to update its contents (step S1403).

Processing in a mouse up event detecting unit 507 will be described next with reference to FIG. 14.

Figure 14:
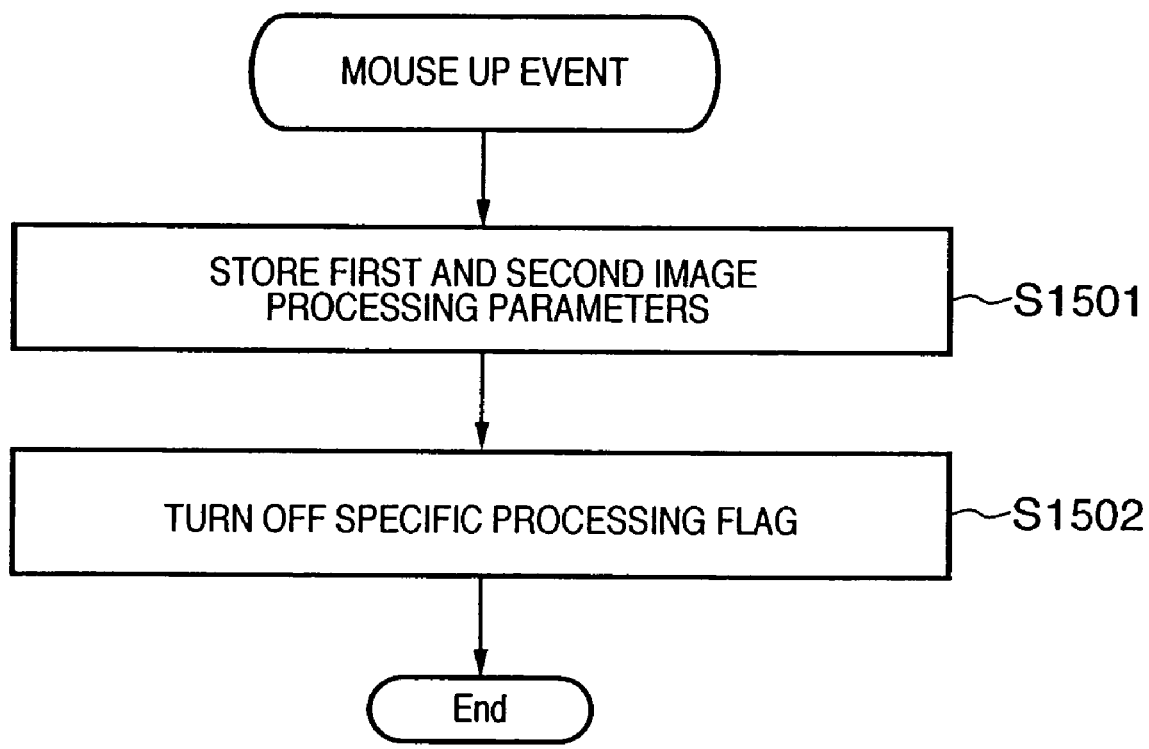
FIG. 14 is a flowchart showing processing in a mouse up event detecting unit according to the fourth embodiment of the present invention.

FIG. 14 is a flowchart showing processing in the mouse up event detecting unit in the axial image display area according to the fourth embodiment.

In the fourth embodiment, when a mouse up event occurs, the X- and Y-direction differences between the current mouse coordinates at this point of time and the start mouse coordinates stored in the storage unit 502 are calculated. First image processing parameters are then calculated by using these differences and stored in the first storage area in the storage unit 502 to update its contents. In addition, the calculated first image processing parameters are stored as second image processing parameters in the second storage area in the storage unit 502 to update its contents (step S1501).

The specific processing flag in the axial image display area is turned on (step S1502).

Note that in the fourth embodiment, as in the first embodiment, the above processing is independently performed for the axial image display area 1002, sagittal image display area 1003, and coronal image display area 1004.

In this case, the specific processing flag is turned on/off individually for each cross section image display area.

If, therefore, the specific processing flag is ON with respect to any one of the cross section image display areas (i.e., if a mouse down event occurs) during a timer processing event, gradation processing is executed in the cross section image display area as a process target in accordance with the first image processing parameters stored in the first storage area in the storage unit 502. In this case, in the cross section image display area as the process target, gradation processing is executed in real time in accordance with a change in mouse drag amount.

In the cross section image display areas other than the cross section image display area as the process target, the specific processing flags are OFF. For this reason, gradation processing is not executed in real time in these cross section image display areas in accordance with a change in mouse drag amount. When the specific processing flag in the cross section image display area as the process target is turned off, i.e., when a mouse up event occurs in the cross section image display area as the process target, gradation processing is executed for the cross section image display areas which are not process targets by using the second image processing parameters stored in the second storage area in the storage unit 502. That is, at this point of time, gradation processing is executed for the remaining cross section image display areas in accordance with the total mouse drag amount.

Note, however, that when dragging operation which has occurred in a given cross section image display area reaches another cross section image display area, the specific processing flag is kept ON, and is turned off at the point of time when a mouse up event finally occurs.

As has been described above, according to the fourth embodiment, in addition to the effects described in the first embodiment, the display methods (sequential updating/displaying of display images and displaying of only final display images) for display images in each cross section image display area can be adaptively switched in accordance with mouse operation (a mouse down event, mouse drag event, and mouse up event) with respect to one of the plurality of cross section image display areas.

Fifth Embodiment

In the first to fourth embodiments, the specific processing flag is ON/OFF-controlled in accordance with the presence/absence of a mouse down event and mouse up event, in particular, as mouse up operation. However, the present invention is not limited to this. For example, the display methods (sequential updating/displaying of display images and displaying of only final display images) for each cross section image display area may be adaptively switched in accordance with the cross section image display area in which the current mouse coordinates as the position indicated by the mouse exist.

In this case, when the mouse enters a given cross section image display area, the specific processing flag is turned on. When the mouse moves in the area and stops for a predetermined period of time in the area or moves outside the area, the specific processing flag is turned off.

With this operation, the display methods (sequential updating/displaying of display images and displaying of only final display images) for each cross section image display area can be adaptively switched in accordance with the moving operation of the cursor (indicating portion) simply indicating the mouse position without any occurrence of a mouse down event, mouse drag event, or mouse up event, and the cross section image display area in which the current mouse coordinates which are the position indicated by the mouse exist.

Sixth Embodiment

In the fourth and fifth embodiments, the above arrangement is used for each cross section image display area. However, the above arrangement may be commonly used for the respective cross section image display areas. In this case, display images are sequentially updated in any cross section image display areas in accordance with a change in mouse drag amount.

In the first to sixth embodiments, the three cross section image display areas are prepared. However, two or three or more cross section image display areas may be prepared in accordance with the application or purpose.

Note that the present invention can be applied to an apparatus comprising a single device or to system constituted by a plurality of devices.

Furthermore, the invention can be implemented by supplying a software program, which implements the functions of the foregoing embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention are implemented by computer, the program code installed in the computer also implements the present invention. In other words, the claims of the present invention also cover a computer program for the purpose of implementing the functions of the present invention.

In this case, so long as the system or apparatus has the functions of the program, the program may be executed in any form, such as an object code, a program executed by an interpreter, or scrip data supplied to an operating system.

Example of storage media that can be used for supplying the program are a floppy disk, a hard disk, an optical disk, a magneto-optical disk, a CD-ROM, a CD-R, a CD-RW, a magnetic tape, a non-volatile type memory card, a ROM, and a DVD (DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functions of the present invention by computer is also covered by the claims of the present invention.

It is also possible to encrypt and store the program of the present invention on a storage medium such as a CD-ROM, distribute the storage medium to users, allow users who meet certain requirements to download decryption key information from a website via the Internet, and allow these users to decrypt the encrypted program by using the key information, whereby the program is installed in the user computer.

Besides the cases where the aforementioned functions according to the embodiments are implemented by executing the read program by computer, an operating system or the like running on the computer may perform all or a part of the actual processing so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

As many apparently widely different embodiments of the present invention can be made without departing from the spirit and scope thereof, it is to be understood that the invention is not limited to the specific embodiments thereof except as defined in the appended claims.

CLAIM OF PRIORITY

This application claims priority from Japanese Patent Application No. 2004-234354 filed on Aug. 11, 2004, the entire contents of which are hereby incorporated by reference herein.

What is claimed is:

1. An image processing apparatus which switches a plurality of images to display an image, comprising:
    a designate unit adapted to designate, as a display range which indicates the images displayed in the plurality of images, start image identification information of a start image of the range and a range image count equivalent to the range, and an image processing range which indicates the images used for image processing for diagnosis;
    a storage unit adapted to store the start image identification information and the range image count as the display range and the image processing range designated by said designate unit;
    an image generation unit adapted to set the images corresponding to each of the images in the display range on the basis of the image processing range, and generate processed images corresponding to the images in the display range by performing image processing on the basis of the set images; and
    a display control unit adapted to switch the display of images including the processed images in the display range on a display unit; and
    a control unit adapted to control a change of the display image range in the plurality of images according to designation of said designate unit, and
    said control unit, if a target image, which does not belong to either of the first display image range before the change and the second display image range after the change, is occurred between the first display range and the second display range, controlling the change of the display image range so as to keep continuity of the displayed images by displaying the target image and then changing to the second display image range after the change.

2. The apparatus according to claim 1, wherein when a change of the start image identification information is to be executed by said designate unit, said control unit controls the change such that an image count from an image corresponding to the start image identification information before the change to an image corresponding to the start image identification information after the change falls within the range image count.

3. The apparatus according to claim 2, wherein when a change of the start image identification information is executed by said designate unit, start image identification information before the change which is stored in said storage unit is updated to start image identification information after the change.

4. The apparatus according to claim 1, further comprising a timer unit adapted to generate a timer event,
    wherein said display control unit repeatedly executes displaying, on said display unit, the processed images consecutively arranged in the range of the range image count while sequentially switching the images in the arranging order of the images in a forward direction in accordance with the timer event.

5. The apparatus according to claim 1, further comprising a timer unit adapted to generate a timer event,
    wherein said display control unit repeatedly and alternately executes displaying, on said display unit, the processed images consecutively arranged in the range of the range image count while sequentially switching the images in the arranging order of the images in a forward direction in accordance with the timer event, and displaying, on said display unit, the processed images while sequentially switching the images in the arranging direction in a backward direction.

6. The apparatus according to claim 1, wherein image processing executed by said image generation unit includes gradation processing and enlargement/reduction processing.

7. The apparatus according to claim 1, wherein
    said designate unit further designates an image processing method for image processing to be executed with respect to images in a predetermined range which includes at least one image of images corresponding to the display range, and
    said image generation unit generates a processed image by performing image processing for the images in the predetermined range by using the image processing method designated by said designate unit.

8. The apparatus according to claim 7, wherein the image processing method includes image processing of generating an average image of images in the predetermined range by performing averaging processing for each of corresponding pixels between the images in the predetermined range.

9. The apparatus according to claim 7, wherein the image processing method includes image processing of generating an MIP (Maximum Intensity Projection) image of a predetermined number of images in the predetermined range by using a maximum pixel value of each of corresponding pixels between the images in the predetermined range.

10. The apparatus according to claim 7, further comprising a timer unit adapted to generate a timer event, wherein said image generation unit sequentially switches images as start images in the predetermined range, performs image processing for images in each predetermined range in which the switched image serves as a start image, and generates a processed image corresponding to each predetermined range, and said display control unit alternately and repeatedly executes displaying, on said display unit, processed images corresponding to said each predetermined range which are arranged in the range of the range image count while sequentially switching the images in an arranging order in a forward direction with respect to a start image in said each predetermined range, and displaying, on said display unit, the images while sequentially switching the images in the arranging order in a backward direction.

11. The apparatus according to claim 1, wherein the plurality of images include at least one cross section images of three cross section images in arbitrary orthogonal directions crossing solid data.

12. The apparatus according to claim 11, further comprising a timer unit adapted to generate a timer event, wherein said image generation unit generates a processed image by performing image processing for each image of at least one cross section images of the three cross section images corresponding to display range stored in said storage unit in accordance with the timer event.

13. A control method for an image processing apparatus which switches a plurality of images to display an image, comprising:

a designating step of designating, as a display range which indicates the images displayed in the plurality of images, start image identification information of a start image of the range and a range image count equivalent to the range, and an image processing range which indicates the images used for image processing for diagnosis;

a storage step of storing the start image identification information and the range image count as the display range and the image processing range designated in the designating step in a storage unit;

an image generating step of setting the images corresponding to each of the images in the display range on the basis of the image processing range, and generating processed images corresponding to the images in the display range by performing image processing on the basis of the set images; and a display control step of switching the display of images including the processed images in the display range on a display unit; and a control step of controlling a change of the display image range in the plurality of images according to designation of said designating step, and said control step, if a target image, which does not belong to either of the first display image range before the change and the second display image range after the change, is occurred between the first display range and the second display range, controlling the change of the display image range so as to keep continuity of the displayed images by displaying the target image and then changing to the second display image range after the change.

* * * * *